US006846492B2

(12) United States Patent
Haap et al.

(10) Patent No.: US 6,846,492 B2
(45) Date of Patent: Jan. 25, 2005

(54) USE OF PHENYLETHYLAMINE DERIVATIVES FOR THE ANTIMICROBIAL TREATMENT OF SURFACES

(75) Inventors: Wolfgang Haap, Grenzach-Wyhlen (DE); Werner Hölzl, Eschentzwiller (FR); Dietmar Ochs, Schopfheim (DE); Karin Petzold, Fischingen (DE); Marcel Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/204,520

(22) PCT Filed: Feb. 13, 2001

(86) PCT No.: PCT/EP01/01561
§ 371 (c)(1),
(2), (4) Date: Aug. 21, 2002

(87) PCT Pub. No.: WO01/62082
PCT Pub. Date: Aug. 30, 2001

(65) Prior Publication Data
US 2003/0207884 A1 Nov. 6, 2003

(30) Foreign Application Priority Data
Feb. 23, 2000 (EP) .............................................. 00810152

(51) Int. Cl.[7] ........................ A01N 25/00; A61K 7/075; A61K 7/50; C11D 7/00; D06L 1/00
(52) U.S. Cl. ........................ 424/405; 510/119; 510/130; 510/276; 514/204; 514/277; 514/312; 514/315; 514/364; 514/365; 514/372; 514/376; 514/384; 514/407; 514/415; 514/445; 514/461; 514/534; 514/649; 514/650; 514/653
(58) Field of Search .......................... 424/405; 510/119, 510/130, 276; 514/204, 277, 312, 315, 364, 365, 372, 376, 384, 407, 415, 445, 461, 534, 649, 650, 653, 269

(56) References Cited

U.S. PATENT DOCUMENTS

| 4,014,937 A | 3/1977 | Richardson | 260/570.8 |
| 4,442,108 A | 4/1984 | Le Polles et al. | 424/258 |
| 4,963,562 A | 10/1990 | Franzmann | 514/307 |
| 5,786,386 A | 7/1998 | Ishida et al. | 514/466 |

FOREIGN PATENT DOCUMENTS

| DE | 1 292 658 | * | 4/1969 |
| EP | 0388320 | | 9/1990 |

OTHER PUBLICATIONS

Camus, L. "The Physiological Action of Hordenine Sulphate" Archives Internationales de Pharmacodynamie et de Therapie, vo XVI, pp. 43–206 (1907).*

Camus, L. "The Physiological Action of Hordenine Sulphate" Archives Internationales de Pharmacodynamie et de Therapie, vo 16, p. 43 (1907). As Abstracted by CAS Online.*
McCleary et al, "Antibiotic Activity of an Extract of Peyote (Lophophora Williamsii (Lemaire) Coulter)" Economic Botany, vol. 14(3), pp. 247–249 (1960).*
Pedrazzoli et Dall'Asta, "Derives des b–hydroxy–alcoylamines II. b–Alcoxy b–phenethylamines substituees sur le noyau benzenique" Chimica Therapeutica, vol. 2(6), pp. 446–451 (1967).*
Kapadia and Fayez, "Peyote Constituents: Chemistry, Biogenesis, and Biological Effects" Journal of Pharmaceutical Sciences, vol. 59(12), pp. 1699–1727 (1970).*
Lenney et al, "Antimicrobial Action of Compound 48/80 against Protozoa, Bacteria, and Fungi" Journal of Pharmaceutical Sciences, vol. 66(5), pp. 702–705 (1977).*

* cited by examiner

Primary Examiner—James O. Wilson
Assistant Examiner—Zachary C. Tucker
(74) Attorney, Agent, or Firm—Kevin T. Mansfield

(57) ABSTRACT

The use of compounds of formula (1) is described, in which compounds $R_1$, $R_2$ and $R_3$ are each independently of the others hydrogen; $C_1$–$C_{20}$alkyl; $C_3$–$C_7$cycloalkyl; $C_2$–$C_{20}$alkenyl; $C_4$–$C_7$cycloalkenyl; $C_2$–$C_{20}$alkynyl, $C_4$–$C_7$cycloalkynyl; or unsubstituted or $C_1$–$C_5$alkyl-, $C_3$–$C_7$cylcoalkyl-, $C_1$–$C_5$alkoxyl-, $C_3$–$C_7$cycloakoxy-, halo-, oxo-, carboxy-, carboxy-$C_1$–$C_7$alkyl ester-, carboxy-$C_3$–$C_7$cylcloalkyl ester-, cyano-, trifluoromethyl-, pentafluoroethyl-, amino-, N,N-mono- or di-$C_1$–$C_{20}$alkylamino- or nitro-substituted phenyl-$C_1$–$C_5$alkyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl; $R_4$, $R_5$, $R_6$ and $R_7$ are each independently of the others hydrogen; $C_1$–$C_{20}$alkyl; $C_3$–$C_7$ cycloalky; $C_2$–$C_{20}$alkenyl; $C_4$–$C_7$ cycloalkenyl; $C_2$–$C_{20}$alkynyl; or $C_4$–$C_7$ cycloalkynyl; and m and n are each independently of the other 0 or 1, for antimicrobial treatment of surfaces. The compounds exhibit a pronounced activity against pathogenic gram-positive and gram-negative bacteria, and also against yeasts and moulds. They are accordingly suitable for the antimicrobial treatment, especially preservation and disinfection, of surfaces.

16 Claims, No Drawings

USE OF PHENYLETHYLAMINE DERIVATIVES FOR THE ANTIMICROBIAL TREATMENT OF SURFACES

"This application was filed under 35 U.S.C. 371, and is the U.S. National Stage of PCT/EP01/01561, filed 23 Feb. 2000."

The present invention relates to the use of selected phenylethylamine derivatives for the antimicrobial treatment of surfaces, as antimicrobial active substances against gram-positive and gram-negative bacteria, yeasts and fungi and also in the preservation of cosmetics, household products, textiles and plastics and for use in disinfectants, and to the preparation of such compounds.

The phenylethylamine derivatives used according to the invention correspond to formula

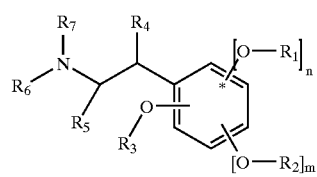

(1)

wherein $R_1$, $R_2$ and $R_3$ are each independently of the others hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; or unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, car-boxy-$C_1$–$C_7$alkyl ester-, carboxy-$C_3$–$C_{12}$cycloalkyl ester-, cyano-, trifluoromethyl-, pentafluoroethyl-, amino-, N,N-mono- or N,N-di-$C_1$–$C_{20}$alkylamino- or nitro-substituted phenyl, phenyl-$C_1$–$C_5$alkyl, biphenyl, biphenyl-$C_1$–$C_5$alkyl, naphthyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl;

$R_4$, $R_5$, $R_6$ and $R_7$ are each independently of the others hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; or $C_4$–$C_{12}$cycloalkynyl; and m and n are each independently of the other 0 or 1.

$C_1$–$C_{20}$Alkyl denotes a straight-chain or branched alkyl radical, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_3$–$C_{12}$Cycloalkyl denotes, for example, cyclopropyl, cyclobutyl, cyclopentyl, cycloheptyl, cyclooctyl, cyclononyl, cyclodecyl, cycloundecyl, cyclodocecyl or especially cyclohexyl.

Alkenyl includes, within the scope of the meanings given, inter alia allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl and n-octadec-4-enyl.

$C_1$–$C_5$Alkoxy denotes a straight-chain or branched radical, e.g. methoxy, ethoxy, propoxy, butoxy or pentyloxy.

According to the invention, preference is given to the use of compounds of formula (I) wherein
$R_4$, $R_5$, $R_6$ and $R_7$ are hydrogen, and especially of compounds of formula (I) wherein
n is 0; and
m is 1.

Special preference is given to compounds of formula

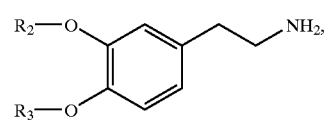

(2)

wherein $R_2$ and $R_3$ are each independently of the other phenyl-$C_1$–$C_5$alkyl unsubstituted or substituted by $C_1$–$C_5$alkyl, $C_2$–$C_6$alkenyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or N,N-di-$C_1$–$C_{20}$alkylamino or by nitro.

According to the invention, special preference is given to the use of compounds of formula (2) wherein
$R_2$ and $R_3$ are $C_1$–$C_5$alkyl or $C_4$–$C_{12}$cycloalkyl.
According to the invention, preference is given also to the use of compounds of formula (2) wherein $R_2$ and $R_3$ are $C_2$–$C_6$alkenyl.

According to the invention, preference is given also to the use of compounds of formula

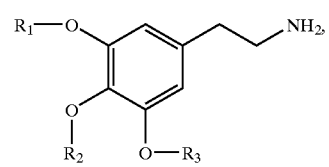

(3)

wherein $R_1$, $R_2$ and $R_3$ are each independently of the others phenylcarbonyl-$C_1$–$C_5$alkyl unsubstituted or substituted by $C_1$–$C_5$alkyl, $C_2$–$C_6$alkenyl, $C_4$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or N,N-di-$C_1$–$C_{20}$alkylamino or by nitro.

Special preference is given to compounds of formula (3) wherein
$R_1$, $R_2$ and $R_3$ are each independently of the others $C_1$–$C_5$alkyl or $C_4$–$C_{12}$cycloalkyl, and also to compounds of formula (3) wherein
$R_1$, $R_2$ and $R_3$ are each independently of the others $C_2$–$C_6$alkenyl.

The following Table 1 lists further examples of phenylethylamine derivatives used according to the invention:

TABLE 1a
General structural formula
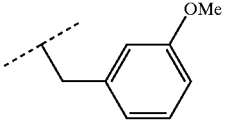
| Compound of formula | $R_1 = R_2$ | Purity [%] (HPLC 214 nm) |
|---|---|---|
| 4 | 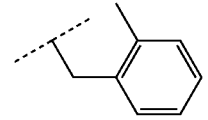 | 96 |
| 5 | 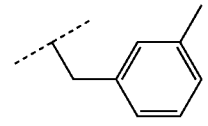 | 95 |
| 6 | 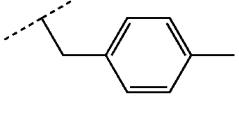 | 95 |
| 7 | 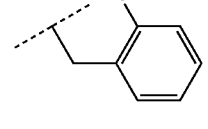 | 95 |
| 8 | 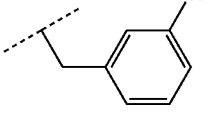 | 85 |
| 9 | 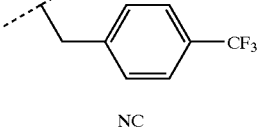 | 99 |
| 10 | 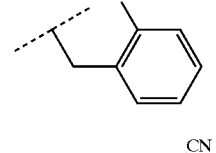 | 99 |
| 11 | 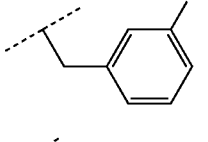 | 99 |
| 12 | 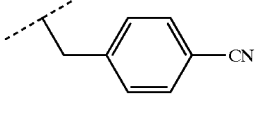 | 99 |
| 13 | 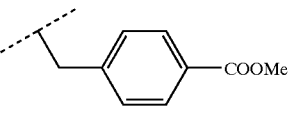 | 99 |
TABLE 1a-continued
General structural formula
| Compound of formula | $R_1 = R_2$ | Purity [%] (HPLC 214 nm) |
|---|---|---|
| 14 | 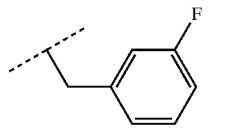 | 99 |
| 15 | 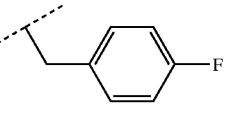 | 97 |
| 16 | 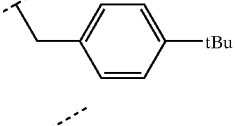 | 99 |
| 17 | 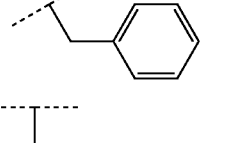 | 82 |
| 18 | 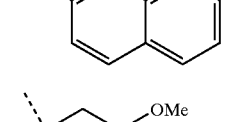 | 94 |
| 19 | 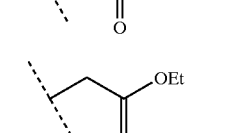 | 91 |
| 20 | 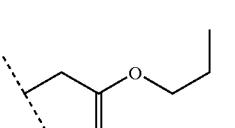 | 94 |
| 21 | 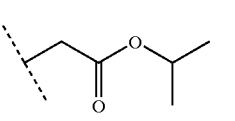 | 91 |
| 22 | 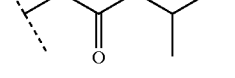 | 98 |
| 23 | | 92 |
| 24 | | 99 |

TABLE 1a-continued

General structural formula $R_1-O-C_6H_3(OR_2)-CH_2CH_2-NH_2$

| Compound of formula | $R_1 = R_2$ | Purity [%] (HPLC 214 nm) |
|---|---|---|
| 25 | -CH₂C(O)O-tBu | 99 |
| 26 | -CH₂C(O)OBzl | 90 |
| 27 | -(CH₂)₃C(O)OEt | 99 |
| 28 | -(CH₂)₄C(O)OEt | 99 |
| 29 | n-propyl | 92 |
| 30 | n-butyl | 98 |
| 31 | isopropyl | 88 |
| 32 | sec-butyl | 99 |
| 33 | isopentyl | 99 |
| 34 | n-pentyl | 84 |
| 35 | 3-pentyl | 88 |
| 36 | n-hexyl | 89 |
| 37 | n-heptyl | 94 |
| 38 | n-octyl | 86 |
| 39 | n-nonyl | 85 |
| 40 | n-decyl | 82 |
| 41 | cyclopentylmethyl | 97 |
| 42 | allyl | 86 |
| 43 | but-3-enyl | 94 |
| 44 | pent-4-enyl | 98 |
| 45 | 3-phenylpropyl | 95 |
| 46 | -CH₂C(O)Ph | 90 |
| 47 | -CH₂C(O)(4-methylphenyl) | 80 |

TABLE 1a-continued

General structural formula

R₁—O— [benzene with ethylamine NH₂]
R₂—O—

| Compound of formula | $R_1 = R_2$ | Purity [%] (HPLC 214 nm) |
|---|---|---|
| 48 | 2-methoxyphenyl propanoyl | 87 |
| 49 | 3-methoxyphenyl propanoyl | 79 |
| 50 | 4-methoxyphenyl propanoyl | 82 |
| 51 | 2,5-dimethoxyphenyl propanoyl | 90 |
| 52 | 4-fluorophenyl propanoyl | 86 |
| 53 | 4-biphenyl propanoyl | 98 |
| 54 | 1-naphthyl propanoyl | 92 |

TABLE 1b

General structural formula

R₁—O— [benzene with ethylamine NH₂]
R₂—O—
O—R₃

| Compound of formula | $R_1 = R_2 = R_3$ | Purity [%] |
|---|---|---|
| 55 | 3-methoxybenzyl | 91 |
| 56 | 2-methylbenzyl | 80 |
| 57 | 3-methylbenzyl | 87 |
| 58 | 4-methylbenzyl | 86 |
| 59 | 2-(trifluoromethyl)benzyl | 99 |
| 60 | 3-(trifluoromethyl)benzyl | 98 |
| 61 | 4-(trifluoromethyl)benzyl | 98 |
| 62 | 2-cyanobenzyl | 96 |
| 63 | 3-cyanobenzyl | 97 |
| 64 | 4-cyanobenzyl | 95 |

TABLE 1b-continued

General structural formula

R₁—O, substituted on benzene ring with $-O-R_2$, $-O-R_3$, and $-CH_2CH_2NH_2$

| Compound of formula | R₁ = R₂ = R₃ | Purity [%] |
|---|---|---|
| 65 | 4-(COOMe)-benzyl | 96 |
| 66 | 2-F-benzyl | 93 |
| 67 | 3-F-benzyl | 94 |
| 68 | 4-F-benzyl | 94 |
| 69 | 4-tBu-benzyl | 96 |
| 70 | benzyl | 94 |
| 71 | 2-naphthylmethyl | 85 |
| 72 | –CH₂C(O)OMe | 99 |
| 73 | –CH₂C(O)OEt | 99 |
| 74 | –CH₂C(O)O-n-propyl | 86 |
| 75 | –CH₂C(O)O-iPr | 96 |
| 76 | –CH₂C(O)O-tBu | 96 |
| 77 | –CH₂C(O)OBzl | 95 |
| 78 | –(CH₂)₃C(O)OEt | 95 |
| 79 | –(CH₂)₄C(O)OEt | 96 |
| 80 | n-propyl | 95 |
| 81 | n-butyl | 99 |
| 82 | isobutyl | 99 |
| 83 | sec-butyl (2-methylbutyl) | 94 |
| 84 | isopentyl | 99 |
| 85 | n-pentyl | 99 |

TABLE 1b-continued
General structural formula
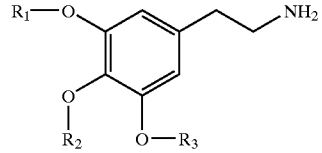
| Compound of formula | $R_1 = R_2 = R_3$ | Purity [%] |
|---|---|---|
| 86 | 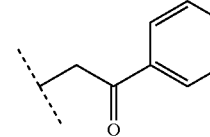 | 99 |
| 87 | | 90 |
| 88 | | 95 |
| 89 | | 98 |
| 90 | | 98 |
| 91 | | 93 |
| 92 | | 93 |
| 93 | | 99 |
| 94 | | 90 |
| 95 | | 98 |
| 96 | | 88 |
| 97 | 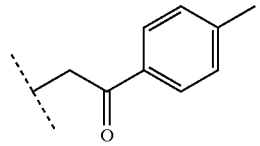 | >99 |
| 98 | | 93 |
| 99 | | >99 |
| 100 | —O—CH$_3$ | n-C$_{12}$H$_{25}$ |
| 101 | H | n-C$_{12}$H$_{25}$ |
| 102 | —O—C$_6$H$_{13}$ | n-C$_6$H$_{13}$ |
The phenylethylamine derivatives used according to the invention are preferably prepared in solid-phase synthesis using a trityl resin according to the following scheme:
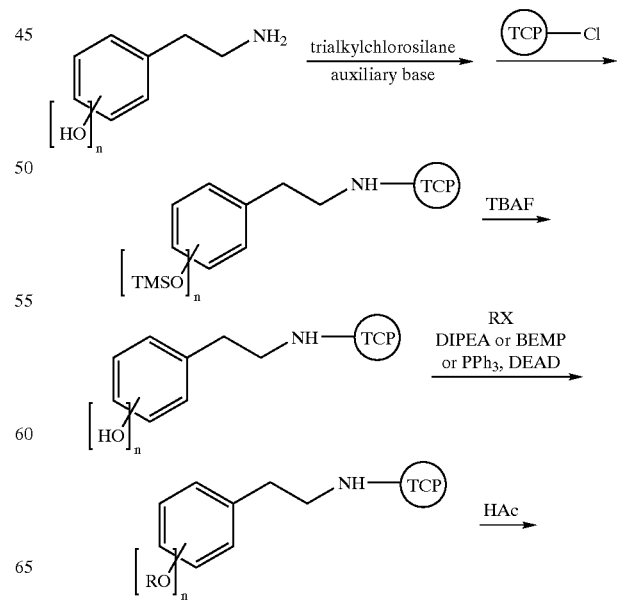

-continued

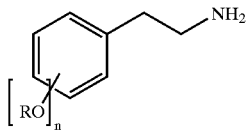

in which

R is $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$-cycloalkynyl; or unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or N,N-di-$C_1$–$C_{20}$alkylamino- or nitro-substituted phenyl, phenyl-$C_1$–$C_5$alkyl, biphenyl, biphenyl-$C_1$–$C_5$alkyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl;

X is F, Cl, Br, I or hydroxy; and n is from 1 to 3.

For that process, 2-(mono-, di- or tri-hydroxyphenyl) ethylamines, such as dopamine or hydroxydopamine hydrochloride, are dissolved in a suitable solvent, for example dichloromethane, DMF, THF, DMA (N,N-dimethylacetamide) or toluene, and an auxiliary base, for example DIPEA (ethyldiisopropylamine) or triethylamine, is added thereto. To that mixture there are added dropwise, per OH group, from 1 to 2 equivalents of a trialkylchlorosilane, for example TMSCl (trimethylsilyl chloride), TIPS-Cl (triisopropylchlorosilane) or TBDMS-Cl (tert-butyldimethylchlorosilane). After stirring for from 1 to 2 hours at a temperature of from 0° C. to 50° C., preferably at 25° C., trityl chloride-polystyrene resin (TCP) or 2-chlorotrityl chloride-polystyrene resin is added.

The resulting suspension is shaken for from S to 20 hours at a temperature of from 0 to 25° C. Unreacted resin is quenched by the addition of methanol. The resin is then washed thoroughly with various solvents (e.g. DMF, methanol, dichloromethane, THF or diethyl ether).

In order to remove the trialkylsilyl groups, the resin is then reacted with 2 equivalents of TBAF (tetrabutylammonium fluoride) in THF over a period of from 1 to 5 hours. The resin is suction-filtered off and washed as described above.

There are three different methods available for alkylating the polymer-bound hydroxyphenylethylamines.

1st method: the loaded resin is shaken with from 10 to 30 equivalents of DIPEA and from 10 to 20 equivalents of a suitable alkyl halide for 16 hours in a suitable solvent, e.g. DMF or dichloromethane, at a temperature of from 0 to 50° C. In order to complete the reaction, the reaction step is repeated.

2nd method: the loaded resin is swelled in a suitable solvent, e.g. DMF or dichloromethane, and from 10 to 20 equivalents of BEMP (2-tert-butylimino-2-diethylamino-1, 3-dimethylperhydro-1,3,2-diazaphosphorin) and from 10 to 20 equivalents of alkyl halide are added thereto. The mixture is shaken for from 10 to 24 hours at a temperature of from 25 to 60° C.

3rd method: the polymer-bound hydroxy groups can also be alkylated by means of a Mitsunobu reaction. For that purpose the resin is swelled in a suitable solvent, e.g. DMF, dichloromethane or THF, and from 2 to 10 equivalents of triphenylphosphine are added. From 2 to 10 equivalents of DEAD, DIAD or azidodicarboxylic acid dipiperidide are then added.

Finally from 2 to 12 equivalents of alcohol are added and shaking is carried out for 24 hours at from 0 to 50° C. The resin is washed and dried as described above.

In order to isolate the end products from the resin, an acid, e.g. trifluoroacetic acid in dichloromethane or a mixture of acetic acid/methanol/dichloromethane, is added to the resin and shaking is carried out for from 1 to 6 hours at 25° C. Filtration is then carried out, and the filtrate is concentrated to dryness in vacuo. The oily residue which remains behind is lyophilised from tert-butyl alcohol/water 4:1.

As an alternative to solid-phase synthesis, some phenyl-ethylamine derivatives, which correspond to the formula

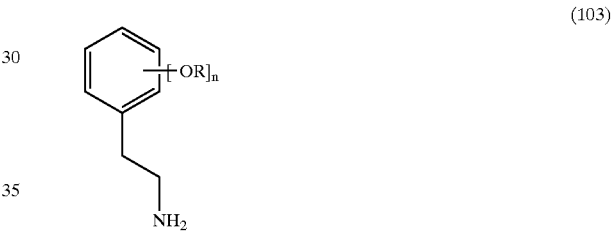

(103)

wherein

R is $C_1$–$C_{20}$alkyl; $C_3$–$C_7$cycloalkyl; or phenyl-$C_1$–$C_5$alkyl unsubstituted or substituted by $C_1$–$C_5$alkyl, $C_3$–$C_7$cycloalkyl, $C_1$–$C_5$alkoxy, $C_3$–$C_7$cycloalkoxy, halogen, oxo, carboxy, carboxy-$C_1$–$C_7$alkyl ester, carboxy-$C_3$–$C_7$cycloalkyl ester, cyano, trifluoromethyl, pentafluoroethyl, amino, N,N-mono- or N,N-di-$C_1$–$C_{20}$alkylamino or by nitro; and n is from 1 to 3;

can be prepared in liquid-phase synthesis by alkylation of an n-hydroxybenzoic acid alkyl ester (step 1), hydrogenation with LiAlH$_4$ to form an alkylated benzyl alcohol (step 2), reaction with thionyl chloride to form the corresponding alkyl halide compound (step 3), reaction with KCN to form the corresponding nitrile compound (step 4) and then reduction with LiAlH$_4$ to form the amino compound of formula (103) (step 5), according to the following scheme:

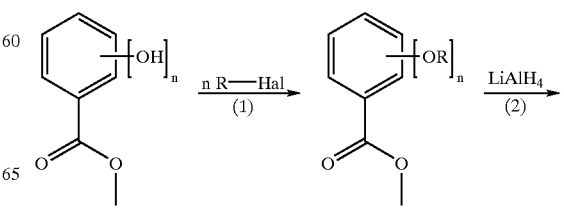

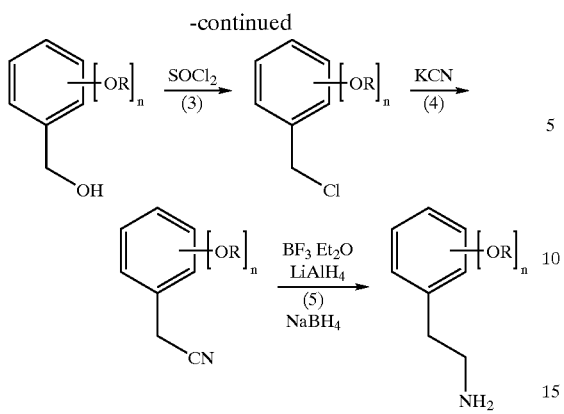

The invention relates also to that process.

The phenylethylamines used according to the invention can also be prepared by alkylation of the deprotonated phenol or mono- or di-hydroxyphenol, subsequent reaction with phosphorus oxychloride and an N,N-dialkylated amide and isolation of the benzaldehyde after hydrolysis (reaction step (1a)), or by reaction of the phenol or mono- or di-hydroxyphenol with phosphorus oxychloride and an N,N-dialkylated amide, alkylation (reaction step (1b)), heating of the aldehyde with a mixture of ammonium acetate and a nitroalkane in a suitable solvent and catalytic hydrogenation of the nitrostyrene to form the phenylethylamine (reaction step (2)), according to the following reaction scheme:

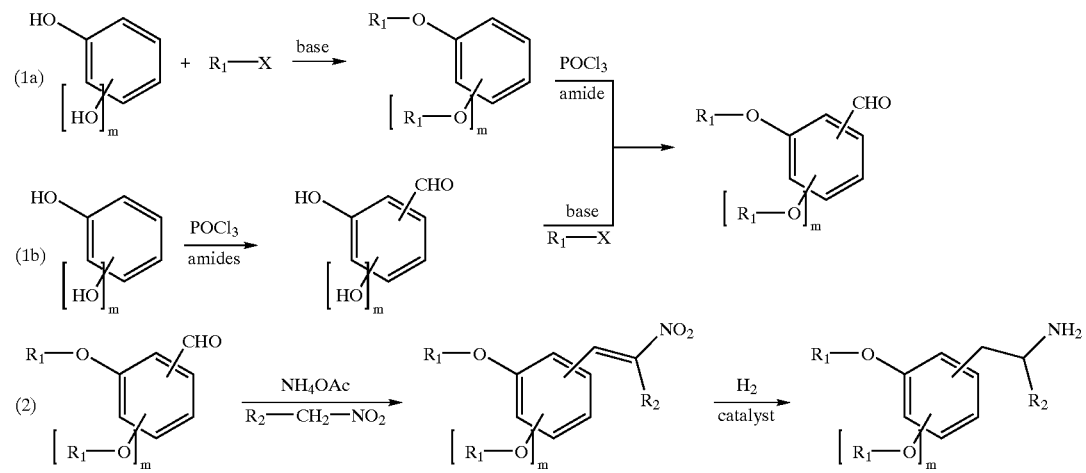

In that reaction scheme $R_1$ and $R_2$ are each independently of the other hydrogen; $C_1$–$C_{20}$alkyl; $C_3$–$C_{12}$cycloalkyl; $C_2$–$C_{20}$-alkenyl; $C_4$–$C_{12}$cycloalkenyl; $C_3$–$C_{20}$alkynyl; $C_4$–$C_{12}$cycloalkynyl; or unsubstituted or $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, carboxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl, phenyl-$C_1$–$C_5$alkyl, biphenyl, biphenyl-$C_1$–$C_5$alkyl, naphthyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl;

X is Cl, Br or I; and m is from 0 to 2.

For the reaction, according to reaction step (1a), phenol or a mono- or di-hydroxyphenol are dissolved in a suitable solvent, e.g. DMF, toluene, xylene, dioxane, etc., and deprotonated with a suitable amount of a base, e.g. NaOH, $Na_2CO_3$, NaOMe, NaOEt, NaOtert-Bu, DIPEA, triethylamine, etc. The appropriate chloride, bromide or iodide ($R_1$-X) is then added dropwise, with heating at from 40 to 120° C. When the reaction is complete, Vilsmeier formylation is carried out according to known procedures. For that purpose the phenyl ether is dissolved in DMF or toluene or xylene etc. (or a mixture of solvents) and reacted with phosphorus oxychloride and an N,N-dialkylated amide, e.g. DMF or dimethylformanilide. After stirring for several hours at a temperature of from −10° C. to 60° C., hydrolysis is carried out and the benzaldehyde is isolated.

Depending upon the phenol, the reaction sequence can also take place in the reverse order (reaction step (1b)).

The preparation of the phenylethylamines (reaction step (2)) is carried out according to the so-called Henry reaction. For that purpose, the aldehyde prepared in reaction step (1a) or (1b) is heated for several hours, at from 30° C. to 100° C., with a mixture of ammonium acetate and a nitroalkane in a suitable solvent. The yellow nitrostyrene formed is then hydrogenated catalytically. For that purpose, the nitrostyrene is dissolved in a suitable solvent, e.g. ethanol, methanol, THF, dioxane or a mixture of solvents, and reduced for several hours in a hydrogenation autoclave under a hydrogen atmosphere of from 1 to 10 bar using a catalyst and at from −15 to 50° C. with the addition of a suitable acid, e.g. hydrochloric acid or sulfuric acid. The phenylethylamine is isolated in hydrochloride or hydrosulfate form.

Alternatively, the nitrostyrene can be reduced with $LiAlH_4$ in a suitable solvent, e.g. diethyl ether, tert-butyl methyl ether or THF, at a temperature of from −45 to 65° C. to form the corresponding phenylethylamine. The hydrochlorides are obtained by dissolution of the phenylethylamines in an inert solvent and reaction with dry hydrogen chloride.

In particular, compounds (100)–(102) can be prepared according to that process.

The phenylethylamine derivatives used according to the invention exhibit pronounced antimicrobial action, especially against pathogenic gram-positive and gram-negative bacteria and against bacteria of the skin flora, and also against yeasts and moulds. They are accordingly suitable especially for disinfection, deodorisation, and for general and antimicrobial treatment of the skin and mucosa and of integumentary appendages (hair), more especially for the disinfection of hands and wounds.

They are accordingly suitable as antimicrobial active ingredients and preservatives in personal care preparations, such as shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation comprising at least one compound of formula (1) and cosmetically tolerable carriers or adjuvants.

The personal care preparation according to the invention contains from 0.01 to 15% by weight, preferably from 0.1 to 10% by weight, based on the total weight of the composition, of a compound of formula (1), and cosmetically tolerable adjuvants.

Depending upon the form of the personal care preparation, it comprises, in addition to the phenylethylamine derivative of formula (1), further constituents, such as sequestering agents, colourings, perfume oils, thickening or solidifying (consistency regulator) agents, emollients, UV-absorbers, skin protective agents, antioxidants, additives that improve the mechanical properties, such as dicarboxylic acids and/or aluminium, zinc, calcium or magnesium salts of $C_{14}$–$C_{22}$ fatty acids, further antimicrobials and, optionally, preservatives.

Typical antimicrobials for combination phenylethylamino derivatives are:

formaldehyde and paraformaldehyde;

hydroxy biphenyls and their salts such as ortho-phenylphenol;

zinc pyrithion;

chlorobutanol;

hydroxy benzoic acids and their salts and esters such as methyl paraben, ethyl paraben, propyl paraben, butyl paraben;

dibromo hexamidine and its salts including isethionate (4,4'-hexamethylenedioxy-bis(3-bromo-benzamidine) and 4,4'-hexamethylenedioxy-bis(3-bromo-benzamidinium 2-hydroxyethanesulfonate);

mercury, (aceto-O)phenyl (i.e. phenyl mercuric acetate) and mercurate(2-),(orthoboate(3-)-O)phenyl, dihydrogen (i.e. phenyl mercuric borate);

1,3-bis(2-ethylhexyl)-hexahydro-5-methyl-5-pyrimidine (hexetidin);

5-bromo-5-nitro-1,3-dioxan;

2-bromo-2-nitro-1,3-propanediol;

2,4-dichlorobenzyl alcohol;

3,4,4' trichlorocarbanilide (trichlorcarban);

p-chloro-m-cresol;

2,4,4'-trichloro-2-hydroxydiphenylether (triclosan);

4,4'-dichloro-2-hydroxydiphenylether;

4-chloro-3,5-dimethylphenol (chloroxylenol);

imidazolidinyl urea;

poly-(hexamethylene biguanide) hydrochloride;

2-phenoxy ethanol (phenoxyethanol);

hexamethylene tetramine (methenamine);

1-(3-chloroallyl)-3,5,7-triaza-1-azonia-adamantane chloride (quaternium 15);

1-(4-chlorophenyoxy)-1-(1-imidazolyl)3,3-dimethyl-2-butanone (climbazole);

1,3-bis(hydroxymethyl)-5,5-dimethyl-2,4-imidazolidinedione (DMDM hydantoin);

benzyl alcohol;

1,2-dibromo-2,4-dicyano butane;

2,2' methylene-bis(6-bromo-4-chloro phenol) (bromochlorophene);

methylchloroisothiazolone, methylisothiazolone, octylisothiazolone, benzylisothiazolone;

2-benzyl-4-chlorophenol (chlorophenone);

chloracetamide;

chlorhexidine, chlorhexidine acetate, chlorhexidine gluconate, chlorhexidine hydrochloride;

1-phenoxy-propane-2-ol (phenoxyisopropanol);

4,4-dimethyl-1,3-oxazolidine (dimethyl oxazolidine);

diazolidinyl urea;

4,4'-hexamethylenedioxybisbenzamidine and 4,4'-hexamethylenedioxybis-(benzamidinium-2-hydroxyethanesulfonate);

glutaraldehyde (1,5-pentanedial);

7-ethylbicyclooxazolidine;

3-(4-chlorophenoxy)-1,2-propanediol (chlorophenesin);

phenylmethoxymethanol and ((phenylmethoxy)methoxy)-methanol (benzylhemiformal)

N-alkyl($C_{12}$–$C_{22}$)trimethyl ammoniumbromide and -chloride (cetrimonium bromide, cetrimonium chloride);

benzyl-dimethyl-(4-(2-(4-(1,1,3,3-tetramethylbutyl)-phenoxy)-ethoxy)-ethyl)-ammoniumchloride (benzethonium chloride);

alkyl-($C_8$–$C_{18}$)-dimethyl-benzylammonium chloride, -bromide and saccharinate;

(benzalkonium chloride, benzalkonium bromide, benzalkonium saccharinate);

benzoic acid and its salts and esters;

propionic acid and its salts;

salicylic acid and its salts;

sorbic acid and its salts;

sodium iodate;

inorganic sulfites and bisulfites such as sodium sulfite;

dehydroacetic acid;

formic acid;

mercurate(1-ethyl)2-mercaptobenzoate(2-)-O,S—, hydrogene (thiomersal or thiomerosal);

10-undecylenic acid and its salts;

octopirox (piroctone olamine);

sodium hydroxy methyl-aminoacetate (sodium hydroxymethylglycinate);

3-iodo-2-propynyl butylcarbamate.

The personal care preparation according to the invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Typical surfactant formulations for cleaning and disinfecting skin, hair, mucous membranes and inanimate surfaces (including textile care) may contain the following ingredients:

anionic, non-ionic, amphoteric, or cationic surfactants;
anionic surfactants can be sulfates such as fatty alcohol sulfates, e.g. sulfated laurylalcohol, fatty acohol ether sulfates such as the acidic esters or their salts of a polymer with 2 to 30 Mol ethylene oxide per mole of a $C_8$–$C_{22}$-fatty alcohol, alkali metals and/or ammonium salts and/or amine salts of $C_8$–$C_{20}$ fatty acids, alkylamide sulfates, alkylamine sulfates (such as monoethanolamine lauryl sulfate), alkylamide ethersulfates, alkylarylpolyethersulfates, monoglyceride sulfates, alkane sulfonates such as those containing alkyl chains with 8 to 20 carbon atoms (e.g. dodecyl sulfonate), alkylamide sulfonates, alkylarylsulfonates, α-olefine sulfonates, sulfosuccinate derivatives (e.g. alkyl sulfosuccinate, alkylethersulfosuccinate or alkylsulfosuccinamide derivatives);

N-[alkylamidoalkyl]amino acids of formula

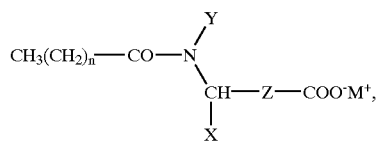

wherein X is a hydrogen, $C_1$–$C_4$-alkyl or —$COO^-M^+$, Y is a hydrogen or $C_1$–$C_4$-alkyl, Z is —$(CH_2)_{m_1-1}$; $m_1$ is 1 to 5, $n_1$ is a number of 6 to 18 and M is an alkali metal- or amine cation;

alkyl- and alkylaryl ethercarboxylates of the formula $CH_3$—X—Y—A, with X is a chain with the general formula —$(CH_2)_{5-19}$—O—,

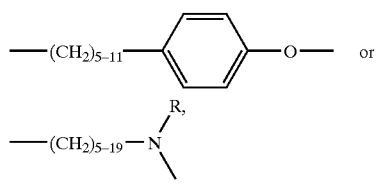

R is a hydrogen or $C_1$–$C_4$-alkyl, Y is —(CH CHO)$_{1-50}$—, A is $(CH_2)_{m2-1}$—$COO^-M^+$ or

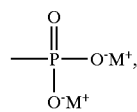

$m_2$ is a number of 1 to 6 and M is an alkali metal- or amine cation.

Moreover anionic surfactants can be fatty acid methyl tauride, alkylisothionate, fatty acid polypeptide condensation products and fatty alcohol phosphoric acid esters. The alkyl radicals in the compounds mentioned above have a C-atom number of typically 8 to 24.

Anionic surfactants are usually used as water-soluble salts such as alkali metal salts, ammonium salts or amine salts. Examples for such salts are lithium salts, sodium salts, potassium salts, ammonium salts, triethanolamine salts, ethanolamine salts, diethanolsamine salts and others.

Particularly the sodium salt, potassium salt and ammonium ($NR_1R_2R_3$)-salt is preferred. $R_1$, $R_2$ and $R_3$ can be hydrogen, $C_1$–$C_4$-alkyl or $C_1$–$C_4$-hydroxyalkyl.

Of particular interest for the formulations are monoethanolamine laurylsulfate or alkali metal salts of fatty alcohol sulfates such as sodium laurylsulfate and sodium laurylethersulfate.

As amphoteric surfactants $C_8$–$C_{18}$-betains, $C_8$–$C_{18}$-sulfobetains, $C_8$–$C_{24}$-alkylamido-$C_1$–$C_4$-alkylene betains, imidazoline carboxylates, alkylamphocarboxycarboxylic acids, alkylamphocarboxylic acid (e.g. lauroamphoglycinate) and N-alkyl-β-aminopropionate or -iminodipropionate can be used.

In particular the $C_{10}$–$C_{20}$-alkylamido$C_1$–$C_4$-alkylenbetaine and coco fatty acid amide propylbetaine.

Non-ionic surfactants can be e.g. derivatives of adducts of propylene oxide/ethylene oxide with a molecular weight of 1,000 to 15,000, fatty alcoholethoxylates (1–50 EO), alkylphenolpolyglycolethers (1–50 EO), polyglucosides, ethoxylated hydrocarbons, fatty acid gly-col(partial)esters such as diethylenglycolmonostearate, fatty acid alkanolamides and -dialkanolamides, fatty acid alkanolamide ethoxylates and fatty amineoxides.

Moreover the salts of saturated and unsaturated $C_8$–$C_{22}$-fatty acids, alone or in combinations with other substances of this group or combinations with other surfactants mentioned above, can be used.

Examples of those fatty acids are capric acid, lauric acid, myristic acid, myristinic acid, palmitic acid, stearic acid, arachidic acid, behenic acid, caproleinic acid, dodecenoic acid, tetradecenoic acid, octadecenoic acid, oleic acid, eicosenic acid, erucic acid as well as combinations thereof such as coco fatty acid. The acids can be used in their salt form, e.g. as alkali metal salts such as sodium salts, potassium salts, or metal salts such as Zn and/or aluminium salts or other alkaline reacting , nitrogen-containing organic compounds such as amines or ethoxylated amines.

These salts can be also produced in situ.

Typical product types are gels (aqueous gels and oleogels), emulsions (w/o systems, o/w systems, water in silicone systems), microemulsions, multiple emulsions (o/w/o and w/o/w systems), sprays (with and without alcohol), sticks (based on synthetic and/or natural soaps), powders, anhydrous creams, oils etc.

Such formulations for personal care, household and laundry care applications may contain raw materials such as preservatives, bactericides and bacteriostatic agents (see list above), perfumes, anti-foaming agents, dyes, pigments, thickening agents, moisturizing agents, humectants, fats, oils, waxes or other typical ingredients of cosmetic and personal care formulations as well as of household products and laundry care products such as alcohols, poly-alcohols, polymers, foam stabilizers, electrolytes, organic solvents, silicone derivatives, emollients, emulsifiers, surfactants, UV absorbers, antioxidants, anti-irritants and anti-inflammatory agents etc.

Antioxidants can be amino acids or amino acid derivatives, imidazoles and their derivatives, peptides such as D,L-carnosine, carotinoids, caroteines and their derivatives, liponic acid, metal chelating agents (such as alpha-hydroxy fatty acids, palmitic acid, phytic acid, lactoferrine), alpha-hydroxyacids (e.g. citric acid, lactic acid, maleic acid), humic acid, gallate, EDTA, EGTA and their derivatives, unsaturated fatty acids and their derivatives, vitamin C and its derivatives, rutinic acid and its derivatives, alpha-glycosyl rutin, ferulic acid, butylhydroxytoluene, butylhydroxyanisole and suitable derivatives of these substances.

Moreover an antioxidant in such formulations might be tetradibutyl pentaerithrityl hydroxy-hydrocinnamate (Tinogard™ TT).

UV absorbers in the formulations might be benzophenone-type substances such as benzophenone-1, benzophenone-2, benzophenone-3 or benzophenone-4 or benzotriazol-type substances such as:

benzenesulfonic acid, 3-(2H-benzotriazol-2-yl)-4-hydroxy-5-(1-methylpropyl)-, monosodium salt;

2-(5-chloro-2H-benzotriazol-2-yl)-6-(1,1-dimethylethyl)-4-methyl-phenol (i.e. bumetrizole);

2-(2H-benzotriazol-2-yl)-6-dodecyl-4-methyl-phenol, branched and linear.

In emulsions, typical emulsifiers used are:

carboxylic acids and their salts such as palmitinic acid, stearic acid, oleic acid, lauric acid etc.;

alkyl phosphates or phosphoric acid esters such as diethanolamine cetyl phosphate, potassium cetyl phosphate etc.;

alkylamines;

alkyl imidazolines;

ethoxylated amines;

quaternary emulsifiers;

sorbitol and sorbitan (polysorbates, sorbitan esters);

sucrose and glucose derivatives such as sorbitan stearate, sucrose cocoate, methyl glucose-sesquistearate, methyl glucose dioleate, methyl glucose isostearate;

alkanolamides and ethoxylated amides such as PEG-n acylamides (with n=1–50);

ethoxylated carboxylic acids or polyethylene glycol esters (PEG-n acylates with n=1–200) such as fatty alcohol polyglycolethers, laureth-n (with n=1–200) ceteareth-n (with n=1–200), -steareth-n (with n=1–100), oleth-n (with n=1–200) and PEG-n stearate (with n=1–200), -PEG-n oleate (with n=1–200), PEG-n cocoate (with n=2–150)

polyglyceryl esters and fatty acid esters;

dimethicone copolyols such as silicone polyethylene oxide copolymer, silicone glycol copolymer;

propoxylated or polyoxyethylene ethers;

polaxamers;

polymeric emulsifiers such as acrylate copolymers or crosspolymers and acrylamides or polyacrylamides;

The lipid phase can be chosen from the following substance groups:

mineral oils, mineral waxes;

oils such as triglycerides of capric and caprylic acid, natural oils such as castor oil;

fats, waxes and other natural and synthetic fats e.g. esters of fatty acids with short chain alcohols such as isopropanol, propylene glycol or glycerin, or esters of fatty alcohols with fatty acids or carboxylic acids with low number of carbon atoms;

alkyl benzoates;

silicone oils such as dimethylpolysiloxane, diethylpolysiloxane, diphenylpolysiloxane or mixtures thereof;

The oil phase of emulsions, oleogels, hydrodispersions or lipodispersions can be chosen from the group of esters of saturated and/or unsaturated, branched and/or linear alkane carboxylic acids with a chain length of 3 to 30 C-atoms and saturated and/or unsaturated, branched or linear alcohols with a chain length of 3 to 30 C-atoms;

from the group of esters of aromatic carboxylic acids and saturated and/or unsaturated, branched and/or linear alcohols with a chain length of 3–30 C-atoms.

Examples of such ester oils are isopropylmyristate, isopropylpalmitate, isopropylstearate, iso-propyloleate, n-butylstearate, n-hexyllaurate, n-decyloleate, isooctylstearate, iso-nonylstearate, isononylisononanoate, 2-ethylhexylpalmitate, 2-hexyllaurate, 2-hexyldecylstearate, 2-octyldodecylpalmitate, oleyloleate, oleylerucate, erucyloleate, erucylerucate as well as synthetic, semi-synthetic and natural mixtures of such esters such as jojoba oil.

The oil phase can be also chosen from the group of saturated and unsaturated hydrocarbons and waxes, silicone oils, dialkylethers, the group of saturated, unsaturated, linear or branched alcohols, fatty acid triglyerides e.g. triglycerin esters of saturated and/or unsaturated, linear and/or branched alkane carboxylic acids with a chain length of 8–24 C-atoms, particularly 12 to 18 C-atoms.

The fatty acid triglycerides can be chosen from the groups of synthetic, semi-synthetic and natural oils e.g. olive oil, sunflower oil, soy oil, peanut oil, rape-seed oil, palm oil, almond oil, coconut oil and similar oils.

Mixtures of such oil and wax components or waxes such as cetyl palmitate can be used as sole oil phase.

Other preferred ingredients in the oil phase are from the group of 2-ethylhexylisostearate, octyldodecanol, isotridecylisononanoate, isoeicosane, 2-ethylhexylcocoate, $C_{12}$–$C_{15}$-alkyl benzoate, caprylic-capric acid-triglycerides and dicaprylic ether or mixtures of those ingredients such as mixtures of 2-ethylhexylisostearate with $C_{12}$–$C_{15}$alkylbenzoate, mixtures of $C_{12}$–$C_{15}$ alkylbenozate and isotridecylisononanoate and mixtures of $C_{12}$–$C_{15}$ alkylbenozate with 2-ethylhexylisostearate and isotridecyl-isononanoate. Moreover cyclic or linear silicone oils can be used and are in some cases the only ingredient in the oil phase. A preferred silicone oil is cyclomethicone (octamethylcyclotetrasiloxane), hexamethylcyclotrisiloxane, polydimethylsiloxane and poly(methylphenyl-siloxane).

From the hydrocarbons the groups of paraffin oil, squalane and squalene are preferred.

The aqueous phase contains for example ingredients such as alcohols, diols or polyols with a low number of C-atoms or their ethers (e.g. ethanol, isopropanol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products).

lower homologues of alcohols such as ethanol, isopropanol, 1,2-dipropanediol, glycerine as well as one or more thickeners for example of the groups of silicon dioxide, aluminium silicates, polysaccharides or derivatives thereof for example hyaluronic acid, xanthan gum, hydroxypropylmethylcellulose, polyacrylates e.g. substances from the Carbopol range (e.g. Carbopol types 980, 981, 1382, 2984, 5984) or Salcare range (Salcare SC80, Salcare SC81, Salcare SC91, Salcare AST, Salcare SC 92, Salcare SC95, Salcare SC96).

Cosmetic formulations according to the invention are used in various fields. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callous-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight of a compound of formula (1)
0.3 to 1% by weight titanium dioxide,
1 to 10% by weight stearic acid,
ad 100% soap base, e.g. a sodium salt of tallow fatty acid or coconut fatty acid, or glycerol.

A shampoo has, for example, the following composition:

0.01 to 5% by weight of a compound of formula (1),
12.0% by weight sodium laureth-2-sulfate,
4.0% by weight cocamidopropyl betaine,
3.0% by weight NaCl and
water ad 100%.

A deodorant has, for example, the following composition:

0.01 to 5% by weight of a compound of formula (1),
60% by weight ethanol,
0.3% by weight perfume oil, and
water ad 100%.

The invention relates also to an oral composition comprising from 0.01 to 15% by weight, based on the total weight of the composition, of a compound of formula (1), and orally tolerable adjuvants.

Example of an oral composition:

10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The phenylethylamino derivatives have a strong antimicrobial activity against oral bacteria and exhibit an antiplaque effectiveness, anti-gingivitis activities and help to reduce paradentitis.

The activity can be improved by combinations with other antimicrobial actives or anti-plaque and anti-gingivitis actives such as chlorhexidine, quaternary compounds such as cetrimonium bromide, benzalkonium chloride and/or phenolic substances such as 2,4,4' trichloro 2'-hydroxy diphenylether, 4,4'-dichloro 2-hydroxy diphenylether, thymol, and other phenolic compounds having the following generic formula:

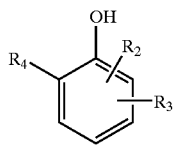

wherein $R_2$, $R_3$ and $R_4$ are independently from each other alkyl (branched, cyclo or linear), aryl, O-aryl, O-alkyl (linear, cyclo, or branched).

Examples are e.g. thymol, 2-tert.-butyl-5-(4-tert.-butylphenyl)-phenol, 2,4-di-t-butyl phenol, 2-cyclohexylmethyl-4-t-butylphenol, 2-t-octyl-5-cyclohexylmethylphenol, 2-t-butyl-4-(1,1-dimethylpropyl)phenol, 2-t-butyl-4-(1,1-dimethylbutyl)phenol, 2,4-di-t-butyl-5-methylphenol, 2-t-butyl-4-(1,1,2,2-tetramethylpropyl)-5-methylphenol, 2-t-butyl-4-(1,1,2,2-tetramethylpropyl)phenol, 2-t-butyl-5-cyclohexylmethylphenol, 2-t-butyl-4-n-heptylphenol, 2-isopropyl-5-cyclohexylmethylphenol, 2-isopropyl-4-cyclohexylmethylphenol, 2-cyclohexyl-4-n-heptylphenol.

Typical oral compositions containing the hydroxy diphenylethers alone or in combinations with one or more of the above mentioned antimicrobials and anti-plaque agents are e.g. mouthrinses, semi-solids such as toothpastes or gel dentifrices, chewing gums or solid lozenges or the like.

Such oral compositions may contain a phenylethylamine derivative or a combination of a phenylethylamine derivative and one or more of the above mentioned antimicrobial and/or anti-plaque compounds.

Furthermore the oral composition may contain:

polishing agents such as silica gels, colloidal silica or complex amorphous alkali metal aluminosilicate, sodium bicarbonate, sodium metaphosphate, potassium metaphosphate, tri-calcium phosphate, dehydrated dicalcium phosphate, anhydrous dicalcium phosphate, calcium pyrophosphate, calcium carbonate, aluminium silicate, hydrated alumina, silica, bentonite and mixtures thereof;

humectants such as glycerin, sorbitol, an alkylene glycol such as polyethylene glycol or propylene glycol and mixtures thereof;

water;

natural or synthetic thickener or gelling agent such as irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose;

alcohol such as ethanol or isopropanol;

organic surface-active agents which can be cationic, anionic or non-ionic;

Typical anionic surface-active agents are water-soluble salts of higher fatty acid monoglyceride monosulfates, such as the sodium salt of the monosulfated monoglycerides of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like.

Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Typical nonionic surface-active agents are condensation products of ethylene oxide with various reactive hydrogen-containing compounds reactive therewith having long hydrophobic chains (e.g. aliphatic chains of about 12–20 carbon atoms), which condensation products ("ethoxamers") contain hydrophilic polyoxyethylene moieties, such as condensation products of poly (ethyleneoxide) with fatty acids, fatty alcohols, fatty amides, polyhydric alcohols (e.g. sorbitan monostearate) and polypropylene oxide (e.g. Pluronic® materials). Polyoxamers are e.g. block copolymers of polyoxyethylene and polyoxypropylene having an average molecular weight from about 3000 to 5000 and a preferred average molecular weight from about 3500 to 4000 and containing about 10–80% hydrophilic polyoxyethylene groups, by weight, of the block copolymer (e.g. Pluronic F127).

flavoring agents such as flavoring oils, e.g. oil of spearmint, peppermint, wintergreen, sassafras, clove, sage, eucalyptus, cinnamon, lemon, orange and methyl salicylate.

sweetening agents such as sucrose, lactose, maltose, xylitol, sodium cyclamate, perillartine, aspartyl phenyl alanine methyl ester, saccharine and the like;

agents used to diminish teeth sensitivity such as strontium chloride, potassium nitrate and potassium citrate;

whitening agents such as urea peroxide and hydrogen peroxide;

preservatives such as sodium benzoate;

substances which release fluoride ions to protect against caries such as inorganic fluoride salts, e.g. sodium, potassium, ammonium or calcium fluoride or organic fluorides such as amine fluoride;

other agents such as chlorophyll compounds and/or ammonium-containing materials such as urea, diammonium phosphate and mixtures thereof.

Antibacterial enhancing agents may be included in the oral composition. Such antibacterial enhancing agents contain a delivery-enhancing group (attaches or substantively, adhesively, cohesively or otherwise bonds the antibacterial enhancing agents with the antibacterial and/or anti-plaque agent to the oral (e.g. tooth and gum) surface) and a retention-enhancing group (generally a hydrophobic group which attaches or otherwise bonds the antimicrobial and/or anti-plaque agent to the antibacterial enhancing agent).

These substances thus deliver the antimicrobial and/or antiplaque agent to the surface and promote retention of the active on the surface which improves the retardation of plaque growth on oral surfaces.

Preferably, the antibacterial enhancing agent is an anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain.

The antibacterial enhancing agent may be a single compound, preferably a polymerizable monomer, more preferably a polymer, including for example oligomers, homopolymers, copolymers, of two or more monomers, ionomers, block copolymers, graft polymers, cross-linked polymers and copolymers, and the like. The antibacterial enhancing agent may be natural or synthetic, and water-soluble or preferably water(saliva)-soluble or -swellable (hydratable, hydrogel-forming) having a (weight) average molecular weight of about 100 to about 5,000,000, preferably about 1000 to about 1,000,000, more preferably about 25,000 to 500,000.

The phenylethylamine derivatives of formula (1) used according to the invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The phenylethylamine derivatives according to the invention are suitable also for treating, especially imparting antimicrobial properties to or preserving, plastics, e.g. polyethylene, polypropylene, polyurethane, polyester, polyamide, polycarbonate, latex, etc. Fields of use therefor are, for example, floor coverings, plastics coatings, plastics container and packaging materials; kitchen and bathroom utensils (e.g. brushes, shower curtains, sponges, bathmats), latex filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the phenylethylamine derivatives according to the invention.

It is also possible for nonwovens, e.g. nappies/diapers, sanitary towels, panty liners, and cloths for hygiene and household uses, to be provided with antimicrobial properties in accordance with the invention.

The phenylethylamine derivatives of formula (1) are also used in washing and cleaning formulations, e.g. in liquid or powder washing agents or softeners.

The phenylethylamine derivatives of formula (1) can be used especially in household and general-purpose cleaners for cleaning and disinfecting hard surfaces.

A cleaning preparation has, for example, the following composition:

0.01 to 5% of a compound of formula (1)
3.0% octyl alcohol 4EO
1.3% fatty alcohol $C_8$–$C_{10}$polyglucoside
3.0% isopropanol
ad 100% water.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or of cellulose derivatives, surface-coatings and paints.

Combinations with chelating agents can also improve the antimicrobial activity of hydroxy diphenylethers. Examples of such chelating agents resulting in additional antimicrobial effects or synergistic activity when combined with hydroxy diphenylethers are ethylene di-amine tetra acetic acid (EDTA), beta-alanine diacetic acid (EDETA), hydroxyethylene di-amino tetraacetic acid, nitrilotriacetic acid (NTA) and ethylenediamine disuccinic acid (S,S-EDDS, R,R-EDDS or S,R-EDDS).

Also combinations of hydroxy diphenylethers such as 4-(2-tert. butyl-5-methylphenoxy)-phenol with perfumes, particularly those containing plant-derived oils, can result in a better antimicrobial efficacy.

Also combinations with natural antimicrobials or chemically modified natural substances with antimicrobial activities such as chitosans and chitosan derivatives, farnesol, plant extracts such as clove oil, blue cypress oil etc. can result in additional antimicrobial effects or even synergistic activities.

The phenylethylamine derivatives of formula (1) are also suitable for the antimicrobial treatment of wood and for the antimicrobial treatment of leather, the preserving of leather and the provision of leather with antimicrobial properties.

The compounds according to the invention are also suitable for the protection of cosmetic products and household products from microbial damage.

The phenylethylamine derivatives that can be used according to the invention are known compounds or new compounds.

The new compounds correspond to formula

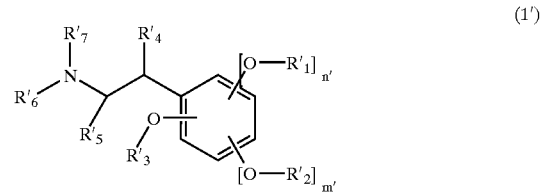

(1')

wherein $R'_1$, $R'_2$ and $R'_3$ are each independently of the others hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; or unsubstituted $C_1$–$C_5$alkyl-, $C_3$–$C_{12}$cycloalkyl-, $C_1$–$C_5$alkoxy-, $C_3$–$C_{12}$cycloalkoxy-, halo-, oxo-, carboxy-, car-boxy-$C_1$–$C_7$alkyl ester-, carboxy-$C_3$–$C_{12}$cycloalkyl ester-, cyano-, trifluoromethyl-, pentafluoroethyl-, amino-, N,N-mono- or di-$C_1$–$C_{20}$alkylamino- or nitro-substituted phenyl or phenyl-$C_1$–$C_5$alkyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl;

$R'_4$, $R'_5$, $R'_6$ and $R'_7$ are each independently of the others hydrogen; $C_1$–$C_{20}$alkyl; $C_3$–$C_{12}$-cycloalkyl; $C_2$–$C_{20}$alkenyl; $C_4$–$C_{12}$cycloalkenyl; $C_3$–$C_{20}$alkynyl; or $C_4$–$C_{12}$cycloalkynyl; an m' and n' are each independently of the other 0 or 1, but do not include those compounds of formula (1') wherein n' is 1; and m' is 0; and simultaneously $R'_1$ and $R'_2$ are $C_1$–$C_5$alkyl, $C_2$–$C_5$alkenyl; benzyl; or a radical of formula (1'a)

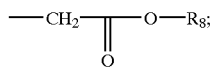

$R'_8$ is $C_1$–$C_4$alkyl;

$R'_4$, $R'_5$, $R'_6$ and $R'_7$ are hydrogen;

or those compounds of formula (1') wherein n' and m' are 1;

$R'_1$, $R'_2$ and $R'_3$ are benzyl; and $R'_4$, $R'_5$, $R'_6$ and $R'_7$ are hydrogen.

The invention relates also to the compounds of formula (1').

The following Examples illustrate the present invention but do not limit it in any way.

General Method for Loading Resin

The compounds of formulae (4) to (102) can be prepared as described below.

EXAMPLE 1

A suspension of dopamine hydrochloride (1.35 g; 7.1 mmol) in absolute dichloromethane (10 ml) and ethyldiisopropylamine (DIPEA, 36 mmol; 5 eq.; 4.6 g; 6.1 ml) is cooled to 0° C. TMSCl (2.2 eq.; 15.6 mmol; 1.69 g; 1.97 ml) is slowly added dropwise. After stirring for 1 hour at 25° C., TCP resin (1.44 mmol/g; 0.3 eq.; 2.4 mmol; 1.67 g) is added. The suspension is shaken for 20 hours at 25° C. Unreacted resin is separated off by the addition of methanol (5 ml). Suction-filtration is then carried out, followed by washing with DMF, MeOH, THF, DCM and $Et_2O$. The resin is dried in vacuo for 1 hour.

EXAMPLE 2

Removal of the TMS Groups

In order to remove the TMS groups, the resin is shaken with a solution of tetrabutyl-ammonium fluoride (TBAF) (2 eq. based on resin loading; 4.8 mmol; 1.25 g) in THF (20 ml) for 1 hour at 25° C. The resin is washed and dried as described in Example 1.

EXAMPLE 3

Alkylation of the OH Groups

Method 1: 25 mg of the dopamine-loaded resin (36 µmol) are suspended in dichloromethane (1 ml), and DIPEA (30 eq.; 1.08 mmol; 140 mg; 185 µl) and alkyl halide (20 eq.; 720 µmol) are added. Shaking is carried out for 16 hours at 25° C. and then the resin is washed as described in Example 1. In order to complete the reaction, the procedure is repeated.

Method 2: 25 mg of the dopamine-loaded resin (36 µmol) are suspended in DMF (1 ml), and BEMP (16 eq.; 576 µmol; 158 mg; 167 µl) and alkyl halide (16 eq.; 576 µmol) are added. Shaking is carried out for 24 hours at 50° C. and then washing is carried out as described in Example 1.

Method 3: 25 mg of the dopamine-loaded resin (36 µmol) are suspended in absolute THF (2 ml), and triphenylphosphine (10 eq.; 360 µmol; 95 mg) is added. Azodicarboxylic acid dipiperidide (10 eq.; 360 µmol; 91 mg) and a suitable alcohol (12 eq.; 432 µmol) are then added. The mixture is shaken for 24 hours at 25° C. and then the resin is washed as described in Example 1.

EXAMPLE 4

Isolation of the Products 25 mg of the dopamine-loaded resin (36 µmol) are suspended in a mixture of acetic acid/methanol/dichloromethane 2:2:6 (2 ml) and the suspension is shaken for 5 hours at 25° C. The solution is filtered and the filtrate is concentrated to dryness in vacuo. The residue is taken up in tert-butyl alcohol/water 4:1 and freeze-dried.

All the products are characterised by ESI-MS and HPLC and exhibit the corresponding protonated products. Some of the compounds are characterised by means of $^1$H- and $^{13}$C-NMR.

Results

|  | Method | Purity of the products [%] (HPLC 214 nm) |
|---|---|---|
| Alkyl halide |  |  |
| ethyl iodide | 1 | 94 |
| isopentyl bromide | 1 | >90 |
| isopentyl bromide | 2 | >99 |
| allyl bromide | 2 | >99 |
| Alcohol |  |  |
| propanol | 3 | 75 |
| butanol | 3 | 83 |
| benzyl alcohol | 3 | 85 |
| 2-phenoxyethanol | 3 | 74 |
| 2-phenylethanol | 3 | 76 |

EXAMPLE 5

Liquid Phase Synthesis of 2-(3,4,5-trisbenzyloxyphenyl)-ethylamine Reaction Scheme

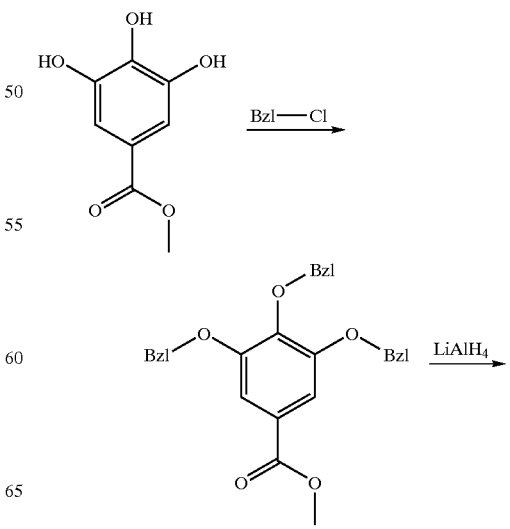

-continued

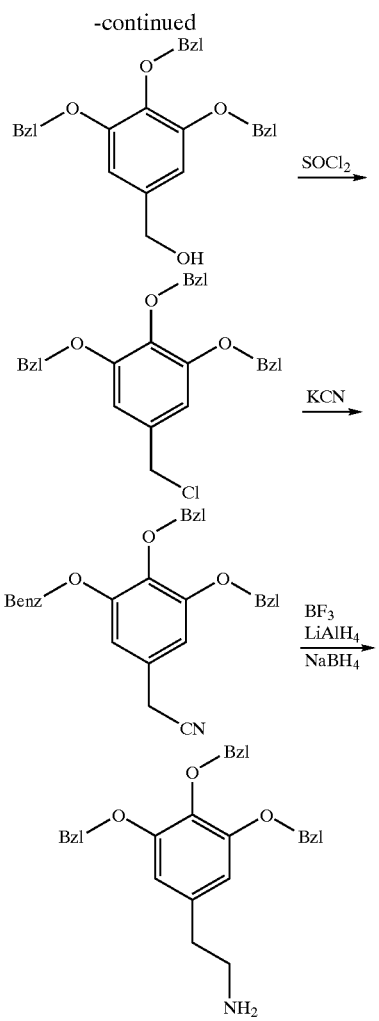

Bzl = benzyl

Literature: A. R. Battersby et al. J. Chem. Soc. Perkin Trans. 1981, 2016 and references cited therein.

EXAMPLE 5a 3.4,5-Trisbenzyloxybenzoic Acid Methyl Ester 105 g (0.83 mol) of benzyl chloride are added dropwise at 56° C., under reflux, over a period of 10 minutes, to 18.4 g (0.1 mol) of 3,4,5-trihydroxybenzoic acid methyl ester, 50.0 g (0.48 mol) of sodium carbonate and 10.0 g (0.06 mol) of potassium iodide in 200 ml of acetone. After a further 20 hours at reflux, 500 ml of water are added at room temperature and the mixture is then extracted with ether. The crude product is worked up in customary manner, excess benzyl chloride is removed by distillation, and the residue is recrystallised from hexane/ethyl acetate. Colourless crystals, yield 45.0 g (98% of theory)

$^1$H-NMR (CDCl$_3$): 3.85 (s,3H, OCH$_3$), 5.05 (s, 2H, OCH$_2$), 5.10 (s, 4H, OCH$_2$), 7.15–7.45 (m, 17H, arom. H)

EXAMPLE 5b 3,4,5-Trisbenzyloxybenzyl Alcohol

A solution of 20.0 g (0.044 mol) of 3,4,5-trisbenzyloxybenzoic acid methyl ester in 100 ml of THF is added dropwise with vigorous stirring, over a period of 60 minutes at room temperature, to a suspension of 4.00 g (0.11 mol) of lithium alanate in 100 ml of THF, in the course of which the temperature rises to 65° C. (reflux). After a further 2 hours at reflux, excess lithium alanate is cautiously hydrolysed, and the product is isolated in customary manner by extraction with methylene chloride. Amorphous powder, yield 12.0 g (64% of theory).

$^1$H-NMR (CDCl$_2$): 1.70 (t, 1H, OH), 4.45 (d, 2H, CH$_2$OH), 4.95 (s, 2H, OCH$_2$), 5.00 (s, 4H, OCH$_2$), 6.55 (s, 2H, arom. H), 7.15–7.40 (m, 15H, arom. H)

EXAMPLE 5c 3,4,5-Trisbenzyloxybenzyl Chloride 40.0 g (0.33 mol) of thionyl chloride are added dropwise at room temperature to a suspension of 12.0 g (0.028 mol) of 3,4,5-trisbenzyloxybenzyl alcohol in 100 ml of diethyl ether. Heating is then carried out at reflux for 2 hours, resulting in a clear solution. After removal of excess thionyl chloride and solvent, the residue is recrystallised from isopropanol/hexane.

Colourless crystals, yield 8.0 g (64% of theory)

$^1$H-NMR (CDCl$_3$): 4.40 (s, 2H, CH$_2$Cl), 4.95 (s, 2H, OCH$_2$), 5.05 (s, 4H, OCH$_2$), 6.60 (s, 2H, arom. H), 7.15–7.35 (m, 15H, arom. H)

EXAMPLE 5d 3,4,5-Trisbenzyloxyphenylacetonitrile

A mixture of 7.0 g (0.015 mol) of 3,4,5-trisbenzyloxybenzyl chloride, 7.0 g (0.1 mol) of potassium cyanide and 1.8 g (0.01 mol) of sodium iodide in 200 ml of acetone is heated at reflux for 18 hours with vigorous stirring. After cooling, 200 ml of water are added, and the product is extracted with chloroform. Recrystallisation from isopropanol yields colourless crystals.

Yield 2.0 g (30% of theory). IR (KBr): v(CN)=2250 cm$^{-1}$

EXAMPLE 5e 2-(3,4,5-Trisbenzyloxyphenyl)-Ethylamine

At room temperature, first a solution of 1.0 g (0.0023 mol) of 3,4,5-trisbenzyloxyphenyl-acetonitrile in 30 ml of THF, and then 10 ml (0.081 mol) of boron trifluoride-diethyl ether complex, are added dropwise to a suspension of 2.5 g (0.067 mol) of sodium borohydride in 20 ml THF. After 2 hours at reflux and cooling, 15 ml of 20% hydrochloric acid and 50 ml of water are added, extraction is carried out with chloroform, and the extract is dried thoroughly with 4A molecular sieve and concentrated by evaporation. After the residue has been taken up in diethyl ether, the hydrochloride is isolated by the introduction of hydrogen chloride.

Hydrochloride: colourless crystals, yield 0.6 g (60% of theory), purity 75% (LC, area % 54 nm), m.p.130° C.

$^1$H-NMR (free amine. CDCl$_3$): 2.80 (t, 2H, PhCH$_2$CH$_2$N), 3.05 (S$_{broad}$, 2H, PhCH$_2$CH$_2$N), 4.90 (s, 2H, OCH$_2$), 5.00 (s, 4H, OCH$_2$), 6.40 (s, 2H, arom. H), 7.10–7.30 (m, 15H, arom. H), 8.15 (S$_{broad}$, 2H, NH$_2$) [M]+. m/z=439u

EXAMPLE 6 a) 4-Dodecyloxy-3-methoxybenzaldehyde

Vanillin (100 g; 0.657 mol) is dissolved in ethanol (500 ml), and dried K$_2$CO$_3$ (101.5 g; 0.73 mol) is added. Heating to 80° C. is then carried out and 1-bromododecane is added dropwise under a protective gas atmosphere. The suspension is heated at reflux for a further 16 hours. After cooling to 25° C., filtration is carried out, the residue is then washed several times with ethanol and the combined filtrates are concentrated to dryness by evaporation. The residue is dissolved in tert-butyl methyl ether. Washing is then carried out with 1M aqueous sodium hydroxide solution (3×200 ml) and water (1×200 ml), and the organic phase is dried over $Na_2SO_4$, filtered off and concentrated to dryness by evaporation.

Yield: 166 g (79%)

b) 1-Nitro-2-(4-dodecyloxy-3-methoxyphenyl)ethene

4-Dodecyloxy-3-methoxybenzaldehyde (166 g; 0.519 mol) is heated for 2 hours at 100° C. with ammonium acetate (20 g; 0.388 mol) and nitromethane (49 ml; 0.914 mol). The resulting melt is then added dropwise with vigorous stirring to methanol, yellow crystals precipitating. After filtration, the residue is washed several times with methanol and then dried.

Yield: 122.3 g (51% based on vanillin) NMR ($\delta$ in ppm; $CDCl_3$): $^1$H-NMR: 8.0 (1H, d, 13.5 Hz); 7.55 (1H, d, 13.5 Hz); 7.18 (1H, d, 8.5 Hz); 7.05 (1H, s); 6.92 (1H, d, 8.5 Hz); 4.10 (2H, t, 7.8 Hz); 3.95 (3H, s); 1.93 (2H, m); 1.51 (2H, m); 1.40 (16H, m); 0.92 (3H, t, 7.8 Hz) $^{13}$C-NMR: 153.0; 150.2; 139.9; 135.4; 125.1; 122.9; 112.8; 111.1; 69.6; 56.5; 32.3; 30.1; 30.03; 29.98; 29.93; 29.75; 29.34; 26.3; 23.10; 14.52 c) 1-Amino-2-(4-dodecyloxy-3-methoxyphenyl)ethane

1-Nitro-2-(4-dodecyloxy-3-methoxyphenyl)ethene (5.7 g; 16 mmol) is suspended in THF ((100 ml) under a protective gas atmosphere. LAH solution (1M in THF; 56 ml, 56 mmol) is then slowly added dropwise. When the addition is complete, heating at reflux is carried out for 2 hours and stirring is then carried out for a further 16 hours at 25° C. Excess LAH is then decomposed with water (8 ml), 15% sodium hydroxide solution (8 ml) and again with water (24 ml). The suspension is stirred for a further 30 minutes at 25° C. and then filtration is carried out. The filtrate is concentrated to dryness by evaporation, and the brown residue is taken up in 10% aqueous hydrochloric acid (12 ml) and washed with tert-butyl methyl ether (3×10 ml). The aqueous phase is rendered alkaline with 15% sodium hydroxide solution (6 ml) and extracted with tert-butyl methyl ether (3×10 ml). The organic extracts are combined, washed with water and saturated sodium chloride solution, and dried over $K_2CO_3$. Filtration is followed by concentration to dryness by evaporation, and freeze-drying is carried out from tert-butyl alcohol/water (4:1) with the addition of hydrochloric acid.

Yield: 1.85 g (12%) NMR ($\delta$ in ppm; DMSO-D6): $^1$H-NMR: 8.1 (2.5 H, broad, NH); 6.88 (1H, d); 6.88 (1H, s); 6.74 (1H, d); 3.93 (2H, t); 3.78 (3H, s); 3.02 (2H, m); 2.82 (2H, m); 1.80 (2H, m); 1.43 (2H, m); 1.30 (16H, m); 0.88 (3H, t) $^{13}$C-NMR ($CDCl_3$): 148.4; 146.6; 127.5; 119.7; 112.1; 111.4; 76.07; 67.97; 54.95; 40.23; 32.14; 30.77; 28.49; 28.31; 28.20; 28.08; 24.84; 21.54; 12.96 MS: $[M+H]^+$ m/z=336

EXAMPLE 7 a) Dodecyloxybenzene

Phenol (47 g; 0.5 mol) is dissolved in DMF (300 ml), and $K_2CO_3$ (82.93 g; 0.6 mol) is added. 1-Bromododecane (124.6 g; 0.5 mol) is then added dropwise to the solution at 70° C. After a further 15 hours at 80° C., cooling to 25° C. is carried out, followed by dilution with water (500 ml) and extraction with tert-butyl methyl ether (2×250 ml). The combined organic extracts are washed with water (2×250 ml) and dried over $Na_2SO_4$. After filtration, concentration to dryness by evaporation is carried out.

Yield: 114 g (86.9%)

b) 4-Dodecyloxybenzaldehyde

Dodecyloxybenzene (2.48 g; 9.45 mmol) is dissolved in N-methylformanilide (195.17 g; 9.45 mmol). $POCl_3$ (1.45 g; 159.33 g; 9.45 mmol) is added dropwise with ice-cooling. Stirring is carried out for 1 hour at 25° C., and then for 3 hours at 60° C. Pouring onto ice is then carried out and the pH is adjusted to 6 using sodium hydroxide solution. Extraction is then carried out with tert-butyl methyl ether (2×50 ml), and the combined organic phases are washed with aqueous $NaHCO_3$ solution and dried over $Na_2SO_4$. After filtration, concentration to dryness by evaporation is carried out.

Yield: 2.72 g (98.9%) NMR ($\delta$ in ppm; DMSO-D6): $^1$H-NMR: 9.82 (1H, s); 7.78 (2H, d, 8.5 Hz); 6.92 (2H, d; 8.5 Hz); 3.97 (2H, t); 1.71 (2H, m); 1.38 (2H, m); 1.20 (16H, m); 0.84 (3H, t) $^{13}$C-NMR: 189.8; 163.1; 131.3; 129.3; 114.0; 67.39; 31.00; 28.81; 28.77; 28.73; 28.52; 28.48; 26.10; 21.73; 13.20 c) 1-Nitro-2-(4-dodecyloxyphenyl)ethene

4-Dodecyloxybenzaldehyde (7.91 g; 27.25 mmol), ammonium acetate (1.57 g; 20.4 mmol) and nitromethane (2.57 ml; 48 mmol) are mixed together and the mixture is heated for 1.5 hours at 105° C. Cooling to 25° C. and extraction with tert-butyl methyl ether (50 ml) are then carried out, and the organic phase is dried over $Na_2SO_4$. After filtration, concentration to dryness by evaporation is carried out and the residue is suspended in methanol (80 ml). Filtration is then carried out, and the pale yellow crystals are washed with methanol and dried in vacuo.

Yield: 4.75 g (52.3%) NMR ($\delta$ in ppm; DMSO-D6): $^1$H-NMR: 8.10 (2H, 2d, 13 Hz); 7.81 (2H, d; 8.5 Hz); 6.99 (2H, d; 8.5 Hz); 4.02 (2H, t); 1.72 (2H, dd); 1.38 (2H, m); 1.28 (16H, m); 0.85 (3h, t) $^{13}$C-NMR: 165.1; 142.5; 138.8; 135.1; 128.5; 125.6; 118.3; 70.9; 34.39; 32.10; 32.06; 31.80; 31.57; 28.49; 25.19; 17.04 d) 1-Amino-2-(4-dodecyloxyphenyl)ethane

Analogous to Example 6c) starting material: 1-nitro-2-(4-dodecyloxyphenyl)ethene (3.33 g; 10 mmol)

Yield: 1.20 g (39.6%) NMR ($\delta$ in ppm; DMSO-D6): $^1$H-NMR: 7.84 (3H, broad, $NH_3$); 7.17 (2H, d, 8.5 Hz); 6.87 (2H, d; 8.5 Hz); 3.90 (2H, t); 3.00 (2H, m); 2.78 (2H, t); 1.69 (2H, m); 1.45 (2H, m); 1.30 (16H, m); 0.87 (3H, t) MS. $[M+H]^+$: m/z=306

EXAMPLE 8 a) 1,2-Dihexyloxybenzene

Pyrocatechol (55.1 g; 0.5 mol) is dissolved in DMF (400 ml), and $K_2CO_3$ (207.3 g) is added. The mixture is heated to 70° C. 1-Bromohexane (198 g; 1.2 mol) is then added dropwise, and heating is carried out for 15 hours at 80° C. Further DMF (400 ml) and water (1 liter) are subsequently added. Extraction is then carried out with tert-butyl methyl ether (2×500 ml), and the organic phase is washed with water (3×100 ml) and dried over $Na_2SO_4$. After filtration, concentration to dryness by evaporation is carried out.

Yield: 137.7 g (98.9%) NMR ($\delta$ in ppm; DMSO-D6): $^1$H-NMR: 6.95 (2H, m); 6.85 (2H, m); 3.92 (4H, t, 7.5 Hz); 1.70 (4H, m); 1.47 (4H, m); 1.35 (8H, m); 0.88 (6H) $^{13}$C-NMR: 149.6; 121.8; 115.0; 69.27; 33.40; 32.08; 26.10; 22.97; 14.70 b) 3,4-Dihexyloxybenzaldehyde 1,2-Dihexyloxybenzene (11.14 g; 40 mmol) and N-methylformanilide (5.41 g; 40 mmol) are cooled to 0° C., and phosphorus oxychloride (6.13 g; 40 mmol) is added. Heating is then carried out for 1 hour at 25° C., followed by stirring for 4 hours at 60° C. The reaction mixture is poured onto ice and then adjusted to pH 6. Extraction is carried out with tert-butyl methyl ether (2×200 ml), and washing is carried out with $NaHCO_3$ (2×100 ml). The organic phase is dried over $Na_2SO_4$, filtered and concentrated to dryness by evaporation.

Yield: 10.8 g (87.8%) NMR (δ in ppm; DMSO-D6):
¹H-NMR: 9.87 (1H, s); 7.55 (1H, d, 8.5 Hz); 7.40 (1H, s); 7.12 (1H, d, 8.5 Hz); 4.17 (2H, t; 7.5 Hz); 4.08 (2H, t; 7.5 Hz); 1.85 (4H, m), 1.48 (4H, m); 1.33 (8H, m); 0.90 (6H, t, 7.5 Hz) ¹³C-NMR: 192.1; 154.9; 149.6; 130.4; 126.7; 126.3; 113.2; 112.1; 69.27; 69.18; 31.83; 31.81; 29.46; 29.35; 26.05; 26.01; 22.95; 14.68 c) 1-Nitro-2-(3,4-dihexyloxyphenyl)ethene 3,4-Dihexyloxybenzaldehyde (122.6 g; 0.4 mmol) is heated to 100° C. with ammonium acetate (23.12 g; 0.3 mol) and nitromethane (42.7 g; 0.7 mol). Working-up is analogous to Example 6b).

Yield: 119.4 9 (85.4%) NMR (δ in ppm; DMSO-D6):
¹H-NMR: 8.25 (1H, d; 13.5 Hz); 8.05 (1H, d; 13.5 Hz); 7.50 (1H, s); 7.39 (1H, d, 8.5 Hz); 7.03 (1H, d, 8.5 Hz); 4.06 (4H, 2t); 1.76 (4H, m); 1.48 (4H, m); 1.35 (8H, m); 0.92 (6H, 2t)
¹³C-NMR: 154.9; 151.3; 142.5; 138.4; 128.3; 125.4; 115.5; 71.07; 70.88; 33.54; 31.21; 31.11; 27.80; 27.74; 24.70; 24.67; 16.45 d) 1-Amino-2-(3,4-dihexyloxyphenyl)ethane

1-Nitro-2-(3,4-dihexyloxyphenyl)ethene (30 g; 85.8 mmol) is dissolved in ethanol with the addition of hydrochloric acid and transferred to a hydrogenation autoclave charged with Pd/C. Cooling is then carried out, and hydrogen is introduced until no further reaction takes place. Filtration is then carried out over a silica gel column, followed by concentration to dryness by evaporation.

Yield: 29.08 g (94.7%) NMR (δ in ppm; DMSO-D6):
¹H-NMR: 8.10 (3H, b; NH₃); 6.87 (2H, d; 8.5 Hz); 6.83 (1H, s); 6.75 (2H, d); 3.93 (4H, 2t); 2.76–3.18 (4H, m); 1.70 (4H, m); 1.42 (4H, m); 1.28 (8H, m); 0.85 (6H, 2t) MS: [M+H]⁺: m/z=322

EXAMPLE 9

Determination of the Minimum Inhibitory Concentration (MIC Value) in Microtiter Plates Nutrient Medium:

Casein/soybean flour peptone bouillon for the preparation of pre-cultures of the test bacteria and yeast.

Mycological slant agar for the pre-culture of moulds

Examples of Test Organisms

| | |
|---|---|
| Bacteria: | *Staphylococcus hominis* DMS 20328 (= SH) |
| | *Staphylococcus aureus* ATCC 9144 |
| | *Staphylococcus epidermidis* ATCC 12228 |
| | *Escherichia coli* NCTC 8196 (= EC) |
| | *Pseudomonas aeruginosa* CIP A-22 (= PA) |
| | *Corynebacterium xerosis* ATCC 373 |
| | *Propionibacterium acnes* ATCC11829 |
| | *Actinomyces viscosum* DSM 43329 |
| | *Streptococcus sobrinus* DSM 20742 |
| | *Streptococcus mutans* ATCC 25175 |
| | *Enterococcus hirae* ATCC 10541 |
| | *Porphyromonas gingivalis* DSM 20709 |
| | *Selenomonas artemidis* ATCC 43528 |
| Yeasts: | *Candida albicans* ATCC 10231 (= CA) |
| | *Malassezia furfur* DSM 6171 |
| Mould: | *Aspergillus niger* ATCC 6275 (= AN) |
| | *Trichophyton mentagrophytes* ATCC 9533 |
| | *Trichophyton rubrum* DSM 4167 |
| | *Epidermophyton floccosum* DSM 10709 |

Procedure:

The test substances are pre-dissolved in dimethyl sulfoxide (DMSO) and tested in a dilution series of 1:2.

Bacteria and yeast are cultured overnight in CASO bouillon, the mould is cultured overnight on mycological slant agar, and washed off with 10 ml of 0.85% sodium chloride solution (+0.1% TritonX-100).

All the test organisms are adjusted to an organism count of 1–5×10⁶ CFU/ml using 0.85% sodium chloride solution.

The test substances are pre-pipetted into microtiter plates in an amount of 8 μl per well.

Pre-diluted organism suspensions are diluted 1:100 in CASO bouillon (bacteria and yeast) or Sabouraud 2% glucose bouillon (mould) and are added in an amount of 192 μl per well to the test substances.

The test batches are incubated for 48 hours at 37° C. (bacteria and yeast) or for 5 days at 28° C. (mould).

After incubation, the growth is evaluated by reference to the turbidity of the test batches (optical density) at 620 nm in a microplate reader.

The minimum inhibitory concentration (MIC value) is the concentration of substance at which (compared with the growth of the control) an appreciable inhibition of growth (≦20% growth) of the test organisms is ascertained.

One microtiter plate is used for each test organism and substance concentration. All the substances are tested in duplicate.

The results are compiled in Table 2:

TABLE 2a

MIC values in ppm for various microorganisms*)

General structural formula

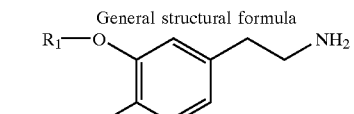

| Compound of formula | R₁ = R₁ | MIC [ppm] SH | MIC [ppm] EC | MIC [ppm] PA | MIC [ppm] CA | MIC [ppm] AN |
|---|---|---|---|---|---|---|
| 4 | 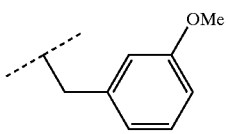 OMe | 30 | 60 | >120 | 60 | 7.5 |

TABLE 2a-continued

MIC values in ppm for various microorganisms*)

General structural formula $R_1-O-\text{C}_6H_3(OR_2)-CH_2CH_2-NH_2$

| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 5 | 2-methylbenzyl | 7.5 | 15 | >120 | 15 | 7.5 |
| 6 | 3-methylbenzyl | 7.5 | 15 | 120 | 7.5 | 120 |
| 7 | 4-methylbenzyl | 3.75 | 7.5 | 120 | 3.75 | >120 |
| 8 | 2-CF$_3$-benzyl | 7.5 | 7.5 | >120 | 15 | >120 |
| 9 | 3-CF$_3$-benzyl | 3.75 | 3.75 | >120 | 7.5 | >120 |
| 10 | 4-CF$_3$-benzyl | 3.75 | 7.5 | >120 | 3.75 | >120 |
| 11 | 2-CN-benzyl | 120 | >120 | >120 | >120 | >120 |
| 12 | 3-CN-benzyl | 60 | 120 | >120 | >120 | 30 |
| 13 | 4-CN-benzyl | 120 | 120 | >120 | >120 | >120 |
| 14 | 4-COOMe-benzyl | 7.5 | 30 | 120 | 30 | >120 |

TABLE 2a-continued

MIC values in ppm for various microorganisms*)

General structural formula $R_1-O-\text{C}_6H_3(-O-R_2)-CH_2CH_2-NH_2$

| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 15 | 2-F-benzyl | 30 | 30 | 120 | 30 | >120 |
| 16 | 3-F-benzyl | 7.5 | 7.5 | 120 | 7.5 | >120 |
| 17 | 4-F-benzyl | 12 | 24 | >120 | 60 | >120 |
| 18 | 4-tBu-benzyl | 1.9 | >60 | >120 | 60 | >120 |
| 19 | benzyl | 28 | 28 | >120 | 60 | >120 |
| 20 | 2-naphthylmethyl | 3.75 | >120 | >120 | >120 | >120 |
| 21 | CH$_2$C(O)OMe | >120 | >120 | >120 | >120 | 120 |
| 22 | CH$_2$C(O)OEt | >120 | >120 | >120 | >120 | >120 |
| 23 | CH$_2$C(O)OPr | >120 | >120 | >120 | >120 | 15 |
| 24 | CH$_2$C(O)OiPr | >120 | >120 | >120 | >120 | 15 |

TABLE 2a-continued
MIC values in ppm for various microorganisms*)
General structural formula
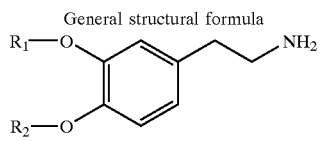
| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 25 | 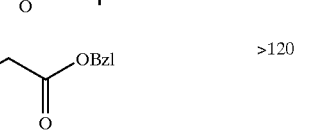 | >120 | >120 | >120 | >120 | 15 |
| 26 | 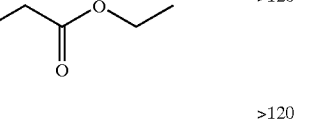 | >120 | >120 | >120 | >120 | >120 |
| 27 |  | >120 | >120 | >120 | >120 | >120 |
| 28 | 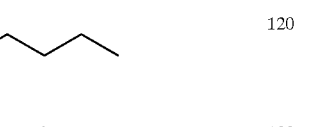 | >120 | >120 | >120 | >120 | >120 |
| 29 |  | >120 | >120 | >120 | >120 | >120 |
| 30 |  | 120 | 120 | >120 | 120 | >120 |
| 31 | 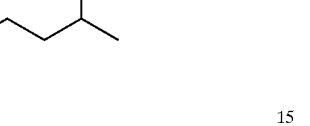 | >120 | >120 | >120 | >120 | >120 |
| 32 |  | >120 | >120 | >120 | >120 | >120 |
| 33 |  | 30 | 15 | 120 | 30 | >120 |
| 34 |  | 15 | 15 | 120 | 15 | >120 |
| 35 | | 60 | 60 | >120 | 60 | >120 |

TABLE 2a-continued
MIC values in ppm for various microorganisms*)
General structural formula
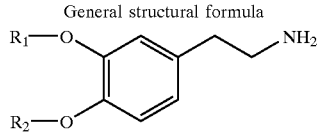
| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 36 | 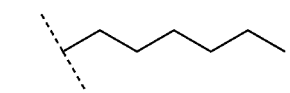 | 3.75 | 3.75 | >120 | 3.75 | >120 |
| 37 | 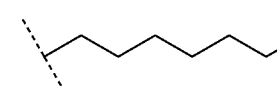 | 3.75 | 30 | >120 | 30 | >120 |
| 38 | 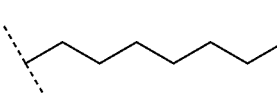 | 7.5 | >120 | >120 | >120 | >120 |
| 39 | 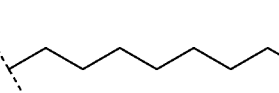 | 60 | >120 | >120 | >120 | >120 |
| 40 | 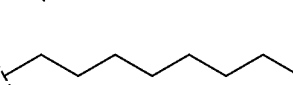 | >120 | >120 | >120 | >120 | >120 |
| 41 | 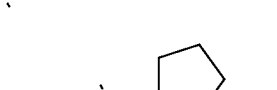 | 120 | 120 | >120 | 120 | >120 |
| 42 |  | >120 | >120 | >120 | >120 | >120 |
| 43 |  | >120 | >120 | >120 | >120 | >120 |
| 44 | 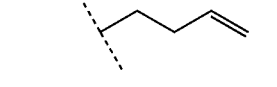 | 60 | 60 | >120 | 60 | >120 |
| 45 | 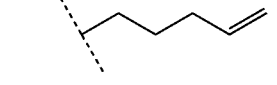 | 15 | 3.75 | >120 | 7.5 | >120 |
| 46 | 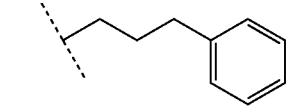 | >100 | >100 | >120 | >120 | >120 |

TABLE 2a-continued
MIC values in ppm for various microorganisms*)
General structural formula
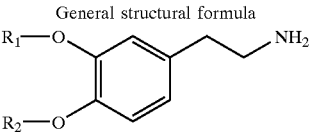
| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 47 | 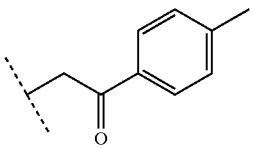 | 60 | 120 | >120 | >120 | >120 |
| 48 | 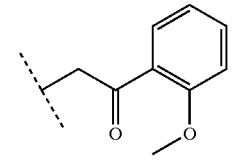 | >52 | >52 | >120 | >120 | 120 |
| 49 | 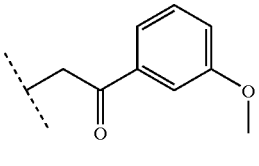 | >120 | >120 | >120 | >120 | >120 |
| 50 | 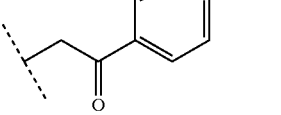 | >120 | >120 | >120 | >120 | >120 |
| 51 | 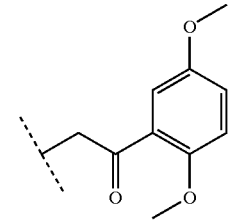 | >120 | >120 | >120 | >120 | >120 |
| 52 | 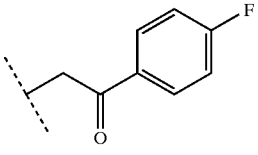 | >120 | 120 | >120 | >120 | 120 |
| 53 | 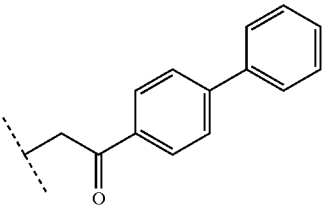 | 3,75 | >120 | >120 | 15 | 30 |

TABLE 2a-continued

MIC values in ppm for various microorganisms*)

General structural formula

R₁—O—[benzene ring]—NH₂
R₂—O—

| Compound of formula | $R_1 = R_1$ | MIC [ppm] SH | MIC [ppm] EC | MIC [ppm] PA | MIC [ppm] CA | MIC [ppm] AN |
|---|---|---|---|---|---|---|
| 54 | (1-naphthyl-C(=O)-CH₂-) | 7.5 | 7.5 | >120 | 15 | 60 |

TABLE 2b

MIC values in ppm for various microorganisms*)

General structural formula

R₁—O—[benzene ring]—NH₂
    O
R₂   O—R₃

| Compound of formula | $R_1 = R_2 = R_3$ | MIC [ppm]SH | MIC [ppm]EC | MIC [ppm]PA | MIC [ppm]CA | MIC [ppm]AN |
|---|---|---|---|---|---|---|
| 55 | 3-methoxybenzyl | 15 | 30 | >120 | >120 | 15 |
| 56 | 2-methylbenzyl | 7.5 | 120 | >120 | 30 | 7.5 |
| 57 | 3-methylbenzyl | 7.5 | >120 | >120 | 30 | >120 |
| 58 | 4-methylbenzyl | 7.5 | >120 | >120 | 15 | 15 |
| 59 | 2-(trifluoromethyl)benzyl | 60 | >120 | >120 | 120 | >120 |

TABLE 2b-continued

MIC values in ppm for various microorganisms*)

General structural formula $$\text{R}_1\text{—O} \diagdown \text{C}_6\text{H}_3(\text{OR}_2)(\text{OR}_3)\text{—CH}_2\text{CH}_2\text{—NH}_2$$

| Compound of formula | $R_1 = R_2 = R_3$ | MIC [ppm]SH | MIC [ppm]EC | MIC [ppm]PA | MIC [ppm]CA | MIC [ppm]AN |
|---|---|---|---|---|---|---|
| 60 | -CH2-C6H4-CF3 (3-CF3) | 30 | >120 | >120 | 120 | >120 |
| 61 | -CH2-C6H4-CF3 (4-CF3) | 60 | >120 | >120 | 120 | >120 |
| 62 | -CH2-C6H4-CN (2-CN) | >120 | >120 | >120 | 60 | 120 |
| 63 | -CH2-C6H4-CN (3-CN) | 120 | >120 | >120 | 60 | >120 |
| 64 | -CH2-C6H4-CN (4-CN) | >120 | >120 | >120 | 60 | 15 |
| 65 | -CH2-C6H4-COOMe (4-COOMe) | 15 | >120 | >120 | 60 | >120 |
| 66 | -CH2-C6H4-F (2-F) | 15 | 15 | >120 | 120 | >120 |
| 67 | -CH2-C6H4-F (3-F) | 3.75 | 7.5 | >120 | 7.5 | >120 |
| 68 | -CH2-C6H4-F (4-F) | 3.75 | 3.75 | >120 | 3.75 | >120 |
| 69 | -CH2-C6H4-tBu (4-tBu) | >120 | >120 | >120 | >120 | >120 |

TABLE 2b-continued
MIC values in ppm for various microorganisms*)
General structural formula
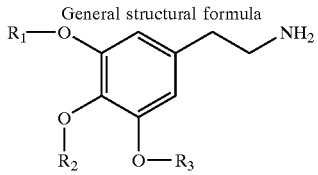
| Compound of formula | $R_1 = R_2 = R_3$ | MIC [ppm]SH | MIC [ppm]EC | MIC [ppm]PA | MIC [ppm]CA | MIC [ppm]AN |
|---|---|---|---|---|---|---|
| 70 | 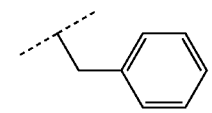 | 7.5 | 7.5 | >120 | 15 | >120 |
| 71 | 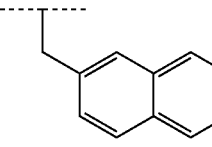 | >120 | >120 | >120 | >120 | >120 |
| 72 | 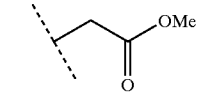 | >120 | >120 | >120 | >120 | >120 |
| 73 | 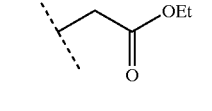 | >120 | >120 | >120 | >120 | >120 |
| 74 | 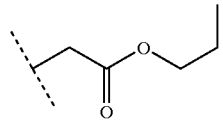 | >120 | >120 | >120 | >120 | >120 |
| 75 | 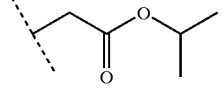 | 60 | >120 | >120 | >120 | >120 |
| 76 | 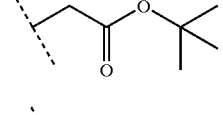 | 21>120 | >120 | >120 | >120 | >120 |
| 77 | 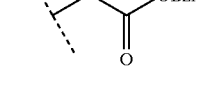 | 120 | >120 | >120 | >120 | >120 |
| 78 | 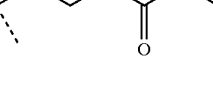 | >120 | >120 | >120 | >120 | >120 |
| 79 | 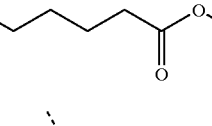 | >120 | >120 | >120 | >120 | 120 |
| 80 | 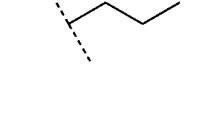 | 120 | 120 | >120 | >120 | 120 |

TABLE 2b-continued

MIC values in ppm for various microorganisms*)

General structural formula $R_1-O-$ ⬡ $-NH_2$, with $O-R_2$ and $O-R_3$ substituents

| Compound of formula | $R_1 = R_2 = R_3$ | MIC [ppm]SH | MIC [ppm]EC | MIC [ppm]PA | MIC [ppm]CA | MIC [ppm]AN |
|---|---|---|---|---|---|---|
| 81 | n-pentyl | 15 | 7,5 | 120 | 30 | >120 |
| 82 | isopropyl | >120 | >120 | >120 | >120 | >120 |
| 83 | sec-butyl | >120 | 30 | >120 | 120 | >120 |
| 84 | isopentyl | 3.75 | 7.5 | >120 | 15 | 15 |
| 85 | n-hexyl | 30 | 15 | >120 | 7.5 | 15 |
| 86 | 3-pentyl | 7.5 | 15 | >120 | 60 | 30 |
| 87 | n-heptyl | 15 | >120 | >120 | >120 | 15 |
| 88 | n-octyl | >120 | >120 | >120 | >120 | >120 |
| 89 | n-nonyl | >120 | >120 | >120 | >120 | >120 |
| 90 | n-decyl | >120 | >120 | >120 | >120 | >120 |

TABLE 2b-continued

MIC values in ppm for various microorganisms*)

General structural formula $R_1-O-\underset{R_2-O\quad O-R_3}{\text{C}_6H_2}-CH_2CH_2-NH_2$

| Compound of formula | $R_1 = R_2 = R_3$ | MIC [ppm]SH | MIC [ppm]EC | MIC [ppm]PA | MIC [ppm]CA | MIC [ppm]AN |
|---|---|---|---|---|---|---|
| 91 | n-decyl | >120 | >120 | >120 | >120 | >120 |
| 92 | cyclopentylmethyl | 15 | 15 | >120 | 60 | 120 |
| 93 | allyl (but-2-enyl) | >120 | >120 | >120 | >120 | >120 |
| 94 | but-3-enyl | 60 | 60 | >120 | 120 | >120 |
| 95 | pent-4-enyl | 15 | 7.5 | 120 | 30 | 120 |
| 96 | 3-phenylpropyl | 7.5 | >120 | >120 | >120 | 60 |
| 97 | 2-oxo-2-phenylethyl | >120 | >120 | >120 | >120 | >120 |
| 98 | 2-oxo-2-(4-methylphenyl)ethyl | 30 | 30 | >120 | >120 | >120 |
| 99 | 2-oxo-2-(4-fluorophenyl)ethyl | 60 | 60 | >120 | >120 | >120 |

*)The MIC values were determined by measuring the optical density at substance concentrations of 120, 60, 30, 15, 7.5 and 3.5 ppm. In that respect, some of the data are approximate values of the activity.

TABLE 2c

MIC values in ppm for various microorganisms

| Microorganism | Compound tested | | |
|---|---|---|---|
| | (100) MIC [ppm] | (101) MIC [ppm] | (102) MIC [ppm] |
| Staphylococcus aureus ATCC 9144 | 25 | 13 | 13 |
| Staphylococcus epidermidis ATCC 12228 | 13 | 13 | 6 |
| Staphylococcus hominis DSM 20328 | 2 | 8 | 4 |
| Corynebacterium xerosis ATCC 373 | 6 | 6 | 6 |
| Propionibacterium acnes ATCC11829 | 50 | — | 13 |
| Actinomyces viscosum DSM 43329 | 25 | — | 13 |
| Streptococcus sobrinus DSM 20742 | 6 | 13 | 6 |
| Enterococcus hirae ATCC 10541 | 25 | 50 | 13 |
| Streptococcus mutans ATCC 25175 | 6 | 6 | 3 |
| Escherichia coli NCTC 8196 | — | — | 4 |
| Pseudomonas aeruginosa CIP A 22 | — | — | — |
| Porphyromonas gingivalis DSM 20709 | 25 | 25 | 2 |
| Selenomonas artemidis ATCC 43528 | — | — | 25 |
| Aspergillus niger ATCC 6275 | 2 | 1 | — |
| Trichophyton mentagrophytes ATCC 9533 | — | — | 25 |
| Trichophyton rubrum DSM 4167 | — | 13 | 25 |
| Epidermophyton floccosum DSM 10709 | 3 | 3 | 6 |
| Malassezia furfur DSM 6171 | — | — | — |
| Candida albicans ATC 10231 | 2 | 50 | 4 |

What is claimed is:

1. A method for the antimicrobial treatment of a surface selected from skin, hair, mucosa, teeth, the mouth, plastics, paper, textile fiber materials, nonwovens, wood or leather, which comprises contacting said surface with an antimicrobially effective amount of a compound of the formula

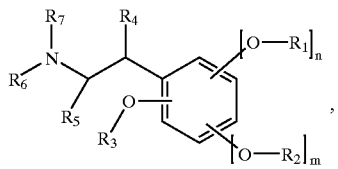

(1)

wherein $R_1$, $R_2$ and $R_3$ are each independently of the others hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; $C_4$–$C_{12}$cycloalkynyl; or phenyl, phenyl-$C_1$–$C_5$alkyl, biphenyl, biphenyl-$C_1$–$C_5$alkyl, naphthyl-$C_1$–$C_5$alkyl, phenylcarbonyl-$C_1$–$C_5$alkyl, naphthylcarbonyl-$C_1$–$C_5$alkyl, pyrrolylalkyl, furanylalkyl, thiophenylalkyl, pyrazolylalkyl, imidazolylalkyl, oxazolylalkyl, thiazolylalkyl, isoxazolylalkyl, isothiazolylalkyl, 1,2,3-triazolylalkyl, 1,2,4-triazolylalkyl, 1,2,3-oxadiazolylalkyl, 1,3,4-oxadiazolylalkyl, 1,2,3-thiadiazolylalkyl, 1,3,4-thiadiazolylalkyl, indolylalkyl, pyridylalkyl, pyridazinylalkyl, pyrimidinylalkyl, pyridazinylalkyl, quinolinylalkyl, isoquinolinylalkyl, pyrrolyl, furanyl, thiophenyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, indolyl, pyridyl, pyridazinyl, pyrimidinyl, pyridazinyl, quinolinyl or isoquinolinyl, each of which is unsubstituted or substituted by $C_1$–$C_5$alkyl, $C_3$–$C_{12}$cycloalkyl, $C_1$–$C_5$alkoxy, $C_3$–$C_{12}$cycloalkoxy, halo, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or nitro;

$R_4$, $R_5$, $R_6$ and $R_7$ are each independently of the others hydrogen; $C_1$–$C_{20}$alkyl; $C_3$–$C_{12}$cycloalkyl; $C_2$–$C_{20}$alkenyl; $C_4$–$C_{12}$cycloalkenyl; $C_3$–$C_{20}$alkynyl; or $C_4$–$C_{12}$cycloalkynyl; and n is 0 or 1; and m is 1.

2. A method according to claim 1, which relates to a compound of formula (1) wherein
$R_4$, $R_5$, $R_6$ and $R_7$ are hydrogen.

3. A method according to claim 1, which relates to a compound of formula

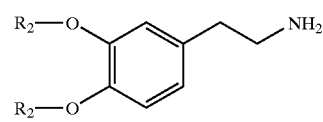

(2)

wherein $R_2$ and $R_3$ are each independently of the other $C_1$–$C_5$alkyl $C_4$–$C_{12}$cycloalkyl or $C_2$–$C_6$alkenyl, phenyl-$C_1$–$C_5$alkyl unsubstituted or substituted by $C_1$–$C_5$alkyl, $C_2$–$C_6$alkenyl, $C_3$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkyl-amino or by nitro.

4. A method according to claim 3, wherein $R_2$ and $R_3$ are $C_1$–$C_5$alkyl or $C_4$–$C_{12}$cycloalkyl.

5. A method according to claim 3, wherein $R_2$ and $R_3$ are $C_2$–$C_6$alkenyl.

6. A method according to claim 1, which relates to a compound of formula

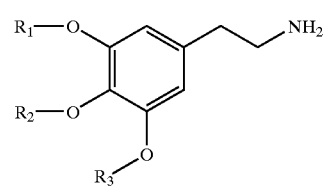

(3)

wherein $R_1$, $R_2$ and $R_3$ are each independently of the others $C_1$–$C_5$alkyl $C_4$–$C_{12}$cycloalkyl or $C_2$–$C_6$alkenyl, phenylcarbonyl-$C_1$–$C_5$alkyl unsubstituted or substituted by $C_1$–$C_5$alkyl, $C_2$–$C_6$alkenyl, $C_4$–$C_{12}$cycloalkyl, $C_1$–$C_5$alkoxy, $C_3$–$C_{12}$cycloalkoxy, halogen, oxo, carboxy, carboxy-$C_1$–$C_7$alkyl ester, carboxy-$C_3$–$C_{12}$cycloalkyl ester, cyano, trifluoromethyl, pentafluoroethyl, amino, N,N-mono- or di-$C_1$–$C_{20}$alkylamino or by nitro.

7. A method according to claim 6, wherein $R_1$, $R_2$ and $R_3$ are each independently of the others $C_1$–$C_5$alkyl or $C_4$–$C_{12}$cycloalkyl.

8. A method according to claim 6, wherein $R_1$, $R_2$ and $R_3$ are each independently of the others $C_2$–$C_6$alkenyl.

9. A method according to claim 1, which comprises the antimicrobial treatment, deodorization and disinfection of the skin, mucosa or hair with a compound of formula (1).

10. A method according to claim 9, which comprises disinfection and deodorization of the skin, mucosa or hair with a compound of formula (1).

11. A method according to claim 1, which comprises treating textile fibre materials with a compound of formula (1).

12. A method according to claim 1, which comprises contacting a substrate to be preserved with a compound of formula (1).

13. A method according to claim 1, which comprises treating textile materials with a washing and cleaning formulation containing an effective amount of a compound of formula (1).

14. A method according to claim 1, which comprises contacting plastics, paper, nonwovens, wood or leather with an antimicrobially and preservatively effective amount of a compound of formula (1).

15. A method according to claim 14, which comprises contacting paper with technical products selected from the group consisting of print thickeners of starch or of cellulose derivatives, surface-coatings and paints, which are preserved and imparted antimicrobial properties by using an antimicrobially and preservatively effective amount of a compound of formula (1).

16. A method according to claim 14, which comprises contacting paper with a biocidally effective amount of a compound of formula (1).

* * * * *